(12) United States Patent
Williams

(10) Patent No.: US 11,344,297 B2
(45) Date of Patent: May 31, 2022

(54) SURGICAL STAPLING DEVICE WITH INDEPENDENTLY MOVABLE JAWS

(71) Applicant: Covidien LP, Mansfield, MA (US)

(72) Inventor: Justin Williams, Southbury, CT (US)

(73) Assignee: Covidien LP, Mansfield, MA (US)

( * ) Notice: Subject to any disclaimer, the term of this patent is extended or adjusted under 35 U.S.C. 154(b) by 127 days.

(21) Appl. No.: 16/777,980

(22) Filed: Jan. 31, 2020

(65) Prior Publication Data

US 2020/0275923 A1 Sep. 3, 2020

Related U.S. Application Data

(60) Provisional application No. 62/811,925, filed on Feb. 28, 2019.

(51) Int. Cl.
*A61B 17/068* (2006.01)
*A61B 17/064* (2006.01)

(52) U.S. Cl.
CPC ........ *A61B 17/068* (2013.01); *A61B 17/0644* (2013.01)

(58) Field of Classification Search
CPC .............. A61B 2017/07214; A61B 2017/0688
USPC ...................................................... 227/175.1
See application file for complete search history.

(56) References Cited

U.S. PATENT DOCUMENTS

| 3,499,591 | A | 3/1970 | Green |
|---|---|---|---|
| 3,777,538 | A | 12/1973 | Weatherly et al. |
| 3,882,854 | A | 5/1975 | Hulka et al. |
| 4,027,510 | A | 6/1977 | Hiltebrandt |
| 4,086,926 | A | 5/1978 | Green et al. |
| 4,241,861 | A | 12/1980 | Fleischer |
| 4,244,372 | A | 1/1981 | Kapitanov et al. |
| 4,429,695 | A | 2/1984 | Green |
| 4,505,414 | A | 3/1985 | Filipi |
| 4,520,817 | A | 6/1985 | Green |
| 4,573,469 | A * | 3/1986 | Golden ................ A61B 17/068 606/220 |
| 4,589,413 | A | 5/1986 | Malyshev et al. |
| 4,596,351 | A | 6/1986 | Fedotov et al. |

(Continued)

FOREIGN PATENT DOCUMENTS

| AU | 198654765 | 9/1986 |
|---|---|---|
| CA | 2773414 A1 | 11/2012 |

(Continued)

OTHER PUBLICATIONS

Extended European Search Report dated Jul. 14, 2020, issued in EP Appln. No. 20159750, 7 pages.

*Primary Examiner* — Gloria R Weeks

(57) ABSTRACT

A surgical stapling device includes an elongate body and a tool assembly. The elongate body has a distal portion and a proximal portion. The tool assembly is supported on the distal portion of the elongate body and includes a stationary jaw, a top jaw positioned on one side of the stationary jaw, and a bottom jaw positioned on an opposite side of the stationary jaw. The top jaw is movable in relation to the stationary jaw independently of the bottom jaw between an open position and a clamped position to clamp tissue between the top jaw and the stationary jaw, and the bottom jaw is movable in relation to the stationary jaw independently of the top jaw between an open position and a clamped position to clamp tissue between the bottom jaw and the stationary jaw.

18 Claims, 15 Drawing Sheets

(56) References Cited

U.S. PATENT DOCUMENTS

| | | |
|---|---|---|
| 4,602,634 A | 7/1986 | Barkley |
| 4,605,001 A | 8/1986 | Rothfuss et al. |
| 4,608,981 A | 9/1986 | Rothfuss et al. |
| 4,610,383 A | 9/1986 | Rothfuss et al. |
| 4,633,861 A | 1/1987 | Chow et al. |
| 4,633,874 A | 1/1987 | Chow et al. |
| 4,671,445 A | 6/1987 | Barker et al. |
| 4,700,703 A | 10/1987 | Resnick et al. |
| 4,703,887 A | 11/1987 | Clanton et al. |
| 4,728,020 A | 3/1988 | Green et al. |
| 4,752,024 A | 6/1988 | Green et al. |
| 4,784,137 A | 11/1988 | Kulik et al. |
| 4,863,088 A | 9/1989 | Redmond et al. |
| 4,869,415 A | 9/1989 | Fox |
| 4,892,244 A | 1/1990 | Fox et al. |
| 4,930,674 A * | 6/1990 | Barak ................. A61B 17/072 227/179.1 |
| 4,955,959 A | 9/1990 | Tompkins et al. |
| 4,978,049 A | 12/1990 | Green |
| 4,991,764 A | 2/1991 | Mericle |
| 5,014,899 A | 5/1991 | Presty et al. |
| 5,031,814 A | 7/1991 | Tompkins et al. |
| 5,040,715 A | 8/1991 | Green et al. |
| 5,065,929 A | 11/1991 | Schulze et al. |
| 5,071,430 A | 12/1991 | de Salis et al. |
| 5,074,454 A | 12/1991 | Peters |
| 5,083,695 A | 1/1992 | Foslien et al. |
| 5,084,057 A | 1/1992 | Green et al. |
| 5,106,008 A | 4/1992 | Tompkins et al. |
| 5,111,987 A | 5/1992 | Moeinzadeh et al. |
| 5,129,570 A | 7/1992 | Schulze et al. |
| 5,141,144 A | 8/1992 | Foslien et al. |
| 5,156,315 A | 10/1992 | Green et al. |
| 5,156,614 A | 10/1992 | Green et al. |
| 5,163,943 A | 11/1992 | Mohiuddin et al. |
| 5,170,925 A | 12/1992 | Madden et al. |
| 5,171,247 A | 12/1992 | Hughett et al. |
| 5,173,133 A | 12/1992 | Morin et al. |
| 5,180,092 A | 1/1993 | Crainich |
| 5,188,274 A | 2/1993 | Moeinzadeh et al. |
| 5,220,928 A | 6/1993 | Oddsen et al. |
| 5,221,036 A | 6/1993 | Takase |
| 5,242,457 A | 9/1993 | Akopov et al. |
| 5,246,156 A | 9/1993 | Rothfuss et al. |
| 5,253,793 A | 10/1993 | Green et al. |
| 5,263,629 A | 11/1993 | Trumbull et al. |
| RE34,519 E | 1/1994 | Fox et al. |
| 5,275,323 A | 1/1994 | Schulze et al. |
| 5,282,807 A | 2/1994 | Knoepfler |
| 5,289,963 A | 3/1994 | McGarry et al. |
| 5,307,976 A | 5/1994 | Olson et al. |
| 5,308,576 A | 5/1994 | Green et al. |
| 5,312,023 A | 5/1994 | Green et al. |
| 5,318,221 A | 6/1994 | Green et al. |
| 5,326,013 A | 7/1994 | Green et al. |
| 5,328,077 A | 7/1994 | Lou |
| 5,330,486 A | 7/1994 | Wilk |
| 5,332,142 A | 7/1994 | Robinson et al. |
| 5,336,232 A | 8/1994 | Green et al. |
| 5,344,061 A | 9/1994 | Crainich |
| 5,352,238 A | 10/1994 | Green et al. |
| 5,356,064 A | 10/1994 | Green et al. |
| 5,358,506 A | 10/1994 | Green et al. |
| 5,364,001 A | 11/1994 | Bryan |
| 5,364,002 A | 11/1994 | Green et al. |
| 5,364,003 A | 11/1994 | Williamson, IV |
| 5,366,133 A | 11/1994 | Geiste |
| 5,376,095 A | 12/1994 | Ortiz |
| 5,379,933 A | 1/1995 | Green et al. |
| 5,381,943 A | 1/1995 | Allen et al. |
| 5,382,255 A | 1/1995 | Castro et al. |
| 5,383,880 A | 1/1995 | Hooven |
| 5,389,098 A | 2/1995 | Tsuruta et al. |
| 5,395,033 A | 3/1995 | Byrne et al. |
| 5,395,034 A | 3/1995 | Allen et al. |
| 5,397,046 A | 3/1995 | Savage et al. |
| 5,397,324 A | 3/1995 | Carroll et al. |
| 5,403,312 A | 4/1995 | Yates et al. |
| 5,405,072 A | 4/1995 | Zlock et al. |
| 5,407,293 A | 4/1995 | Crainich |
| 5,413,268 A | 5/1995 | Green et al. |
| 5,415,334 A | 5/1995 | Williamson et al. |
| 5,415,335 A | 5/1995 | Knodell, Jr. |
| 5,417,361 A | 5/1995 | Williamson, IV |
| 5,423,471 A | 6/1995 | Mastri et al. |
| 5,425,745 A | 6/1995 | Green et al. |
| 5,431,322 A | 7/1995 | Green et al. |
| 5,431,323 A | 7/1995 | Smith et al. |
| 5,433,721 A | 7/1995 | Hooven et al. |
| 5,441,193 A | 8/1995 | Gravener |
| 5,441,494 A * | 8/1995 | Ortiz ........................ B25J 3/00 294/213 |
| 5,445,304 A | 8/1995 | Plyley et al. |
| 5,447,265 A | 9/1995 | Vidal et al. |
| 5,452,837 A | 9/1995 | Williamson, IV et al. |
| 5,456,401 A | 10/1995 | Green et al. |
| 5,464,300 A | 11/1995 | Crainich |
| 5,465,895 A | 11/1995 | Knodel et al. |
| 5,467,911 A | 11/1995 | Tsuruta et al. |
| 5,470,007 A | 11/1995 | Plyley et al. |
| 5,470,010 A | 11/1995 | Rothfuss et al. |
| 5,472,132 A | 12/1995 | Savage et al. |
| 5,474,566 A | 12/1995 | Alesi et al. |
| 5,476,206 A | 12/1995 | Green et al. |
| 5,478,003 A | 12/1995 | Green et al. |
| 5,480,089 A | 1/1996 | Blewett |
| 5,482,197 A | 1/1996 | Green et al. |
| 5,484,095 A | 1/1996 | Green et al. |
| 5,484,451 A | 1/1996 | Akopov et al. |
| 5,485,947 A | 1/1996 | Olson et al. |
| 5,485,952 A | 1/1996 | Fontayne |
| 5,486,185 A | 1/1996 | Freitas et al. |
| 5,487,499 A | 1/1996 | Sorrentino et al. |
| 5,487,500 A | 1/1996 | Knodel et al. |
| 5,489,058 A | 2/1996 | Plyley et al. |
| 5,490,856 A | 2/1996 | Person et al. |
| 5,497,933 A | 3/1996 | DeFonzo et al. |
| 5,501,689 A * | 3/1996 | Green ................. A61B 17/0686 227/19 |
| 5,505,363 A | 4/1996 | Green et al. |
| 5,507,426 A | 4/1996 | Young et al. |
| 5,518,163 A | 5/1996 | Hooven |
| 5,518,164 A | 5/1996 | Hooven |
| 5,529,235 A | 6/1996 | Boiarski et al. |
| 5,531,744 A | 7/1996 | Nardella et al. |
| 5,535,934 A | 7/1996 | Boiarski et al. |
| 5,535,935 A | 7/1996 | Vidal et al. |
| 5,535,937 A | 7/1996 | Boiarski et al. |
| 5,540,375 A | 7/1996 | Bolanos et al. |
| 5,542,594 A | 8/1996 | McKean et al. |
| 5,549,628 A | 8/1996 | Cooper et al. |
| 5,551,622 A | 9/1996 | Yoon |
| 5,553,765 A | 9/1996 | Knodel et al. |
| 5,554,164 A | 9/1996 | Wilson et al. |
| 5,554,169 A | 9/1996 | Green et al. |
| 5,560,530 A | 10/1996 | Bolanos et al. |
| 5,560,532 A | 10/1996 | DeFonzo et al. |
| 5,562,239 A | 10/1996 | Boiarski et al. |
| 5,562,241 A | 10/1996 | Knodel et al. |
| 5,562,682 A | 10/1996 | Oberlin et al. |
| 5,562,701 A | 10/1996 | Huitema et al. |
| 5,564,615 A | 10/1996 | Bishop et al. |
| 5,571,116 A | 11/1996 | Bolanos et al. |
| 5,573,169 A | 11/1996 | Green et al. |
| 5,573,543 A | 11/1996 | Akopov et al. |
| 5,575,799 A | 11/1996 | Bolanos et al. |
| 5,575,803 A | 11/1996 | Cooper et al. |
| 5,577,654 A | 11/1996 | Bishop |
| 5,584,425 A | 12/1996 | Savage et al. |
| 5,586,711 A | 12/1996 | Plyley et al. |
| 5,588,580 A | 12/1996 | Paul et al. |
| 5,588,581 A | 12/1996 | Conlon et al. |
| 5,597,107 A | 1/1997 | Knodel et al. |
| 5,601,224 A | 2/1997 | Bishop et al. |

(56) References Cited

U.S. PATENT DOCUMENTS

| | | | |
|---|---|---|---|
| 5,607,095 A | 3/1997 | Smith et al. | |
| 5,615,820 A | 4/1997 | Viola | |
| 5,618,291 A | 4/1997 | Thompson et al. | |
| 5,624,452 A | 4/1997 | Yates | |
| 5,626,587 A | 5/1997 | Bishop et al. | |
| 5,628,446 A | 5/1997 | Geiste et al. | |
| 5,630,539 A | 5/1997 | Plyley et al. | |
| 5,630,540 A | 5/1997 | Blewett | |
| 5,630,541 A | 5/1997 | Williamson, IV et al. | |
| 5,632,432 A | 5/1997 | Schulze et al. | |
| 5,634,584 A | 6/1997 | Okorocha et al. | |
| 5,636,780 A | 6/1997 | Green et al. | |
| 5,645,209 A | 7/1997 | Green et al. | |
| 5,647,526 A | 7/1997 | Green et al. | |
| 5,651,491 A | 7/1997 | Heaton et al. | |
| 5,653,373 A | 8/1997 | Green et al. | |
| 5,653,374 A | 8/1997 | Young et al. | |
| 5,653,721 A | 8/1997 | Knodel et al. | |
| 5,655,698 A | 8/1997 | Yoon | |
| 5,657,921 A | 8/1997 | Young et al. | |
| 5,658,300 A | 8/1997 | Bito et al. | |
| 5,662,258 A | 9/1997 | Knodel et al. | |
| 5,662,259 A | 9/1997 | Yoon | |
| 5,662,260 A | 9/1997 | Yoon | |
| 5,662,662 A | 9/1997 | Bishop et al. | |
| 5,662,666 A | 9/1997 | Onuki et al. | |
| 5,665,085 A | 9/1997 | Nardella | |
| 5,667,517 A | 9/1997 | Hooven | |
| 5,669,544 A | 9/1997 | Schulze et al. | |
| 5,673,840 A | 10/1997 | Schulze et al. | |
| 5,673,841 A | 10/1997 | Schulze et al. | |
| 5,673,842 A | 10/1997 | Billner et al. | |
| 5,676,674 A | 10/1997 | Bolanos et al. | |
| 5,680,981 A | 10/1997 | Mililli et al. | |
| 5,680,982 A | 10/1997 | Schulze et al. | |
| 5,680,983 A | 10/1997 | Plyley et al. | |
| 5,690,269 A | 11/1997 | Bolanos et al. | |
| 5,690,675 A | 11/1997 | Sawyer et al. | |
| 5,692,668 A | 12/1997 | Schulze et al. | |
| 5,697,542 A | 12/1997 | Knodel et al. | |
| 5,702,409 A | 12/1997 | Rayburn et al. | |
| 5,704,534 A | 1/1998 | Huitema et al. | |
| 5,706,997 A | 1/1998 | Green et al. | |
| 5,709,334 A | 1/1998 | Sorrentino et al. | |
| 5,711,472 A | 1/1998 | Bryan | |
| 5,713,505 A | 2/1998 | Huitema | |
| 5,713,919 A * | 2/1998 | Lahr | A61B 17/29 606/205 |
| 5,715,988 A | 2/1998 | Palmer | |
| 5,716,366 A | 2/1998 | Yates | |
| 5,718,359 A | 2/1998 | Palmer et al. | |
| 5,725,536 A | 3/1998 | Oberlin et al. | |
| 5,725,554 A | 3/1998 | Simon et al. | |
| 5,728,110 A | 3/1998 | Vidal et al. | |
| 5,732,806 A | 3/1998 | Foshee et al. | |
| 5,735,848 A | 4/1998 | Yates et al. | |
| 5,743,456 A | 4/1998 | Jones et al. | |
| 5,749,893 A | 5/1998 | Vidal et al. | |
| 5,752,644 A | 5/1998 | Bolanos et al. | |
| 5,752,965 A * | 5/1998 | Francis | A61B 17/07207 227/178.1 |
| 5,762,255 A | 6/1998 | Chrisman et al. | |
| 5,762,256 A | 6/1998 | Mastri et al. | |
| 5,769,303 A | 6/1998 | Knodel et al. | |
| 5,769,892 A | 6/1998 | Kingwell | |
| 5,772,099 A | 6/1998 | Gravener | |
| 5,772,673 A | 6/1998 | Cuny et al. | |
| 5,776,075 A * | 7/1998 | Palmer | A61B 10/06 600/564 |
| 5,779,130 A | 7/1998 | Alesi et al. | |
| 5,779,131 A | 7/1998 | Knodel et al. | |
| 5,779,132 A | 7/1998 | Knodel et al. | |
| 5,782,396 A | 7/1998 | Mastri et al. | |
| 5,782,397 A | 7/1998 | Koukline | |
| 5,782,834 A | 7/1998 | Lucey et al. | |
| 5,785,232 A | 7/1998 | Vidal et al. | |
| 5,797,536 A | 8/1998 | Smith et al. | |
| 5,797,537 A | 8/1998 | Oberlin et al. | |
| 5,797,538 A | 8/1998 | Heaton et al. | |
| 5,810,811 A | 9/1998 | Yates et al. | |
| 5,810,855 A | 9/1998 | Rayburn et al. | |
| 5,814,055 A | 9/1998 | Knodel et al. | |
| 5,814,057 A | 9/1998 | Oi et al. | |
| 5,816,471 A | 10/1998 | Plyley et al. | |
| 5,817,109 A | 10/1998 | McGarry et al. | |
| 5,820,009 A | 10/1998 | Melling et al. | |
| 5,823,066 A | 10/1998 | Huitema et al. | |
| 5,826,776 A | 10/1998 | Schulze et al. | |
| 5,829,662 A | 11/1998 | Allen et al. | |
| 5,833,695 A | 11/1998 | Yoon | |
| 5,836,147 A | 11/1998 | Schnipke | |
| 5,862,972 A | 1/1999 | Green et al. | |
| 5,865,361 A | 2/1999 | Milliman et al. | |
| 5,871,135 A | 2/1999 | Williamson, IV et al. | |
| 5,873,873 A | 2/1999 | Smith et al. | |
| 5,878,938 A | 3/1999 | Bittner et al. | |
| 5,893,506 A | 4/1999 | Powell | |
| 5,894,979 A | 4/1999 | Powell | |
| 5,897,562 A | 4/1999 | Bolanos et al. | |
| 5,901,895 A | 5/1999 | Heaton et al. | |
| 5,911,352 A | 6/1999 | Racenet et al. | |
| 5,911,353 A | 6/1999 | Bolanos et al. | |
| 5,918,791 A | 7/1999 | Sorrentino et al. | |
| 5,919,198 A | 7/1999 | Graves, Jr. et al. | |
| 5,922,001 A | 7/1999 | Yoon | |
| 5,931,847 A | 8/1999 | Billner et al. | |
| 5,941,442 A | 8/1999 | Geiste et al. | |
| 5,954,259 A | 9/1999 | Viola et al. | |
| 5,964,774 A | 10/1999 | McKean et al. | |
| 5,980,510 A | 11/1999 | Tsonton et al. | |
| 5,988,479 A | 11/1999 | Palmer | |
| 6,004,335 A | 12/1999 | Vaitekunas et al. | |
| 6,010,054 A | 1/2000 | Johnson et al. | |
| 6,032,849 A | 3/2000 | Mastri et al. | |
| 6,045,560 A | 4/2000 | McKean et al. | |
| 6,063,097 A | 5/2000 | Oi et al. | |
| 6,079,606 A | 6/2000 | Milliman et al. | |
| 6,099,551 A | 8/2000 | Gabbay | |
| 6,109,500 A | 8/2000 | Alli et al. | |
| 6,131,789 A | 10/2000 | Schulze et al. | |
| 6,131,790 A | 10/2000 | Piraka | |
| 6,155,473 A | 12/2000 | Tompkins et al. | |
| 6,197,017 B1 | 3/2001 | Brock et al. | |
| 6,202,914 B1 | 3/2001 | Geiste et al. | |
| 6,241,139 B1 | 6/2001 | Milliman et al. | |
| 6,250,532 B1 | 6/2001 | Green et al. | |
| 6,264,086 B1 | 7/2001 | McGuckin, Jr. | |
| 6,264,087 B1 | 7/2001 | Whitman | |
| 6,279,809 B1 | 8/2001 | Nicolo | |
| 6,315,183 B1 | 11/2001 | Piraka | |
| 6,315,184 B1 | 11/2001 | Whitman | |
| 6,325,810 B1 | 12/2001 | Hamilton et al. | |
| 6,330,965 B1 | 12/2001 | Milliman et al. | |
| 6,391,038 B2 | 5/2002 | Vargas et al. | |
| 6,398,797 B2 | 6/2002 | Bombard et al. | |
| 6,436,097 B1 | 8/2002 | Nardella | |
| 6,439,446 B1 | 8/2002 | Perry et al. | |
| 6,443,973 B1 | 9/2002 | Whitman | |
| 6,478,804 B2 | 11/2002 | Vargas et al. | |
| 6,488,196 B1 | 12/2002 | Fenton, Jr. | |
| 6,503,257 B2 | 1/2003 | Grant et al. | |
| 6,505,768 B2 | 1/2003 | Whitman | |
| 6,544,274 B2 | 4/2003 | Danitz et al. | |
| 6,554,844 B2 | 4/2003 | Lee et al. | |
| 6,565,554 B1 | 5/2003 | Niemeyer | |
| 6,587,750 B2 | 7/2003 | Gerbi et al. | |
| 6,592,597 B2 | 7/2003 | Grant et al. | |
| 6,594,552 B1 | 7/2003 | Nowlin et al. | |
| 6,602,252 B2 | 8/2003 | Mollenauer | |
| 6,619,529 B2 | 9/2003 | Green et al. | |
| D480,808 S | 10/2003 | Wells et al. | |
| 6,638,285 B2 * | 10/2003 | Gabbay | A61B 17/072 606/139 |
| 6,644,532 B2 | 11/2003 | Green et al. | |

(56) References Cited

U.S. PATENT DOCUMENTS

| | | |
|---|---|---|
| 6,656,193 B2 | 12/2003 | Grant et al. |
| 6,669,073 B2 | 12/2003 | Milliman et al. |
| 6,681,978 B2 | 1/2004 | Geiste et al. |
| 6,698,643 B2 | 3/2004 | Whitman |
| 6,716,232 B1 | 4/2004 | Vidal et al. |
| 6,722,552 B2 | 4/2004 | Fenton, Jr. |
| 6,755,338 B2 | 6/2004 | Hahnen et al. |
| 6,783,524 B2 | 8/2004 | Anderson et al. |
| 6,786,382 B1 | 9/2004 | Hoffman |
| 6,817,509 B2 | 11/2004 | Geiste et al. |
| 6,830,174 B2 | 12/2004 | Hillstead et al. |
| 6,835,199 B2 | 12/2004 | McGuckin, Jr. et al. |
| 6,843,403 B2 | 1/2005 | Whitman |
| RE38,708 E | 3/2005 | Bolanos et al. |
| 6,874,669 B2 * | 4/2005 | Adams ............ A61B 17/072 227/175.1 |
| 6,877,647 B2 | 4/2005 | Green et al. |
| 6,889,116 B2 | 5/2005 | Jinno |
| 6,905,057 B2 | 6/2005 | Swayze et al. |
| 6,945,444 B2 | 9/2005 | Gresham et al. |
| 6,953,138 B1 | 10/2005 | Dworak et al. |
| 6,953,139 B2 | 10/2005 | Milliman et al. |
| 6,959,852 B2 | 11/2005 | Shelton, IV et al. |
| 6,962,594 B1 | 11/2005 | Thevenet |
| 6,964,363 B2 | 11/2005 | Wales et al. |
| 6,978,921 B2 | 12/2005 | Shelton, IV et al. |
| 6,981,628 B2 | 1/2006 | Wales |
| 6,986,451 B1 | 1/2006 | Mastri et al. |
| 6,988,649 B2 | 1/2006 | Shelton, IV et al. |
| 6,991,627 B2 | 1/2006 | Madhani et al. |
| 6,994,714 B2 | 2/2006 | Vargas et al. |
| 7,000,818 B2 | 2/2006 | Shelton, IV et al. |
| 7,000,819 B2 | 2/2006 | Swayze et al. |
| 7,032,799 B2 | 4/2006 | Viola et al. |
| 7,044,352 B2 | 5/2006 | Shelton, IV et al. |
| 7,044,353 B2 | 5/2006 | Mastri et al. |
| 7,055,730 B2 | 6/2006 | Ehrenfels et al. |
| 7,055,731 B2 | 6/2006 | Shelton, IV et al. |
| 7,059,508 B2 | 6/2006 | Shelton, IV et al. |
| 7,070,083 B2 | 7/2006 | Jankowski |
| 7,083,075 B2 | 8/2006 | Swayze et al. |
| 7,097,089 B2 | 8/2006 | Marczyk |
| 7,111,769 B2 | 9/2006 | Wales et al. |
| 7,114,642 B2 | 10/2006 | Whitman |
| 7,121,446 B2 | 10/2006 | Arad et al. |
| 7,128,253 B2 | 10/2006 | Mastri et al. |
| 7,128,254 B2 | 10/2006 | Shelton, IV et al. |
| 7,140,527 B2 | 11/2006 | Ehrenfels et al. |
| 7,140,528 B2 | 11/2006 | Shelton, IV |
| 7,143,923 B2 | 12/2006 | Shelton, IV et al. |
| 7,143,924 B2 | 12/2006 | Scirica et al. |
| 7,143,925 B2 | 12/2006 | Shelton, IV et al. |
| 7,143,926 B2 | 12/2006 | Shelton, IV et al. |
| 7,147,138 B2 | 12/2006 | Shelton, IV |
| 7,159,750 B2 | 1/2007 | Racenet et al. |
| 7,168,604 B2 | 1/2007 | Milliman et al. |
| 7,172,104 B2 | 2/2007 | Scirica et al. |
| 7,188,758 B2 | 3/2007 | Viola et al. |
| 7,207,471 B2 | 4/2007 | Heinrich et al. |
| 7,213,736 B2 | 5/2007 | Wales et al. |
| 7,225,963 B2 | 6/2007 | Scirica |
| 7,225,964 B2 | 6/2007 | Mastri et al. |
| 7,238,195 B2 | 7/2007 | Viola |
| 7,246,734 B2 | 7/2007 | Shelton, IV |
| 7,258,262 B2 | 8/2007 | Mastri et al. |
| 7,267,682 B1 | 9/2007 | Bender et al. |
| 7,278,562 B2 | 10/2007 | Mastri et al. |
| 7,278,563 B1 | 10/2007 | Green |
| 7,287,682 B1 | 10/2007 | Ezzat et al. |
| 7,293,685 B2 | 11/2007 | Ehrenfels et al. |
| 7,296,722 B2 | 11/2007 | Ivanko |
| 7,296,724 B2 | 11/2007 | Green et al. |
| 7,296,772 B2 | 11/2007 | Wang |
| 7,300,444 B1 | 11/2007 | Nielsen et al. |
| 7,303,107 B2 | 12/2007 | Milliman et al. |
| 7,303,108 B2 | 12/2007 | Shelton, IV |
| 7,308,998 B2 | 12/2007 | Mastri et al. |
| 7,326,232 B2 | 2/2008 | Viola et al. |
| 7,328,828 B2 | 2/2008 | Ortiz et al. |
| 7,328,829 B2 | 2/2008 | Arad et al. |
| 7,334,717 B2 | 2/2008 | Rethy et al. |
| 7,354,447 B2 | 4/2008 | Shelton, IV et al. |
| 7,357,287 B2 | 4/2008 | Shelton, IV et al. |
| 7,364,061 B2 | 4/2008 | Swayze et al. |
| 7,367,485 B2 | 5/2008 | Shelton, IV et al. |
| 7,377,928 B2 * | 5/2008 | Zubik ............ A61B 17/072 606/151 |
| 7,380,695 B2 | 6/2008 | Doll et al. |
| 7,380,696 B2 | 6/2008 | Shelton, IV et al. |
| 7,396,356 B2 | 7/2008 | Mollenauer |
| 7,398,907 B2 | 7/2008 | Racenet et al. |
| 7,399,310 B2 | 7/2008 | Edoga et al. |
| 7,401,720 B1 | 7/2008 | Durrani |
| 7,401,721 B2 | 7/2008 | Holsten et al. |
| 7,404,508 B2 | 7/2008 | Smith et al. |
| 7,404,509 B2 | 7/2008 | Ortiz et al. |
| 7,407,074 B2 | 8/2008 | Ortiz et al. |
| 7,407,075 B2 | 8/2008 | Holsten et al. |
| 7,407,077 B2 | 8/2008 | Ortiz et al. |
| 7,407,078 B2 | 8/2008 | Shelton, IV et al. |
| 7,416,101 B2 | 8/2008 | Shelton, IV et al. |
| 7,419,080 B2 | 9/2008 | Smith et al. |
| 7,419,081 B2 | 9/2008 | Ehrenfels et al. |
| 7,419,495 B2 | 9/2008 | Menn et al. |
| 7,422,139 B2 | 9/2008 | Shelton, IV et al. |
| 7,424,965 B2 | 9/2008 | Racenet et al. |
| 7,431,189 B2 | 10/2008 | Shelton, IV et al. |
| 7,431,730 B2 | 10/2008 | Viola |
| 7,434,715 B2 | 10/2008 | Shelton, IV et al. |
| 7,434,717 B2 | 10/2008 | Shelton, IV et al. |
| 7,438,208 B2 | 10/2008 | Larson |
| 7,438,209 B1 | 10/2008 | Hess et al. |
| 7,441,684 B2 | 10/2008 | Shelton, IV et al. |
| 7,441,685 B1 | 10/2008 | Boudreaux |
| 7,448,525 B2 | 11/2008 | Shelton, IV et al. |
| 7,451,904 B2 | 11/2008 | Shelton, IV |
| 7,455,208 B2 | 11/2008 | Wales et al. |
| 7,455,676 B2 | 11/2008 | Holsten et al. |
| 7,458,494 B2 | 12/2008 | Matsutani et al. |
| 7,461,767 B2 | 12/2008 | Viola et al. |
| 7,462,185 B1 | 12/2008 | Knodel |
| 7,464,846 B2 | 12/2008 | Shelton, IV et al. |
| 7,464,847 B2 | 12/2008 | Viola et al. |
| 7,464,848 B2 | 12/2008 | Green et al. |
| 7,464,849 B2 | 12/2008 | Shelton, IV et al. |
| 7,467,740 B2 | 12/2008 | Shelton, IV et al. |
| 7,472,814 B2 | 1/2009 | Mastri et al. |
| 7,472,815 B2 | 1/2009 | Shelton, IV et al. |
| 7,472,816 B2 | 1/2009 | Holsten et al. |
| 7,473,258 B2 | 1/2009 | Clauson et al. |
| 7,481,347 B2 | 1/2009 | Roy |
| 7,481,348 B2 | 1/2009 | Marczyk |
| 7,481,349 B2 | 1/2009 | Holsten et al. |
| 7,481,824 B2 | 1/2009 | Boudreaux et al. |
| 7,487,899 B2 | 2/2009 | Shelton, IV et al. |
| 7,490,749 B2 | 2/2009 | Schall et al. |
| 7,494,039 B2 | 2/2009 | Racenet et al. |
| 7,500,979 B2 | 3/2009 | Hueil et al. |
| 7,503,474 B2 | 3/2009 | Hillstead et al. |
| 7,506,790 B2 | 3/2009 | Shelton, IV |
| 7,506,791 B2 | 3/2009 | Omaits et al. |
| 7,510,107 B2 | 3/2009 | Timm et al. |
| 7,513,408 B2 | 4/2009 | Shelton, IV et al. |
| 7,517,356 B2 | 4/2009 | Heinrich |
| 7,537,602 B2 | 5/2009 | Whitman |
| 7,543,729 B2 | 6/2009 | Ivanko |
| 7,543,730 B1 | 6/2009 | Marczyk |
| 7,543,731 B2 | 6/2009 | Green et al. |
| 7,552,854 B2 | 6/2009 | Wixey et al. |
| 7,556,185 B2 | 7/2009 | Viola |
| 7,556,186 B2 | 7/2009 | Milliman |
| 7,559,450 B2 | 7/2009 | Wales et al. |
| 7,559,452 B2 | 7/2009 | Wales et al. |
| 7,559,453 B2 | 7/2009 | Heinrich et al. |

(56) References Cited

U.S. PATENT DOCUMENTS

| | | | |
|---|---|---|---|
| 7,559,937 B2 * | 7/2009 | de la Torre | A61B 17/07207 227/176.1 |
| 7,565,993 B2 | 7/2009 | Milliman et al. | |
| 7,568,603 B2 | 8/2009 | Shelton, IV et al. | |
| 7,568,604 B2 | 8/2009 | Ehrenfels et al. | |
| 7,571,845 B2 | 8/2009 | Viola | |
| 7,575,144 B2 | 8/2009 | Ortiz et al. | |
| 7,584,880 B2 | 9/2009 | Racenet et al. | |
| 7,588,174 B2 | 9/2009 | Holsten et al. | |
| 7,588,175 B2 | 9/2009 | Timm et al. | |
| 7,588,176 B2 | 9/2009 | Timm et al. | |
| 7,588,177 B2 | 9/2009 | Racenet | |
| 7,597,229 B2 | 10/2009 | Boudreaux et al. | |
| 7,597,230 B2 | 10/2009 | Racenet et al. | |
| 7,600,663 B2 | 10/2009 | Green | |
| 7,604,150 B2 | 10/2009 | Boudreaux | |
| 7,604,151 B2 | 10/2009 | Hess et al. | |
| 7,607,557 B2 | 10/2009 | Shelton, IV et al. | |
| 7,611,038 B2 | 11/2009 | Racenet et al. | |
| 7,617,961 B2 | 11/2009 | Viola | |
| 7,624,902 B2 | 12/2009 | Marczyk et al. | |
| 7,624,903 B2 | 12/2009 | Green et al. | |
| 7,631,793 B2 | 12/2009 | Rethy et al. | |
| 7,631,794 B2 | 12/2009 | Rethy et al. | |
| 7,635,073 B2 | 12/2009 | Heinrich | |
| 7,635,074 B2 | 12/2009 | Olson et al. | |
| 7,635,373 B2 | 12/2009 | Ortiz | |
| 7,637,409 B2 | 12/2009 | Marczyk | |
| 7,637,410 B2 | 12/2009 | Marczyk | |
| 7,641,091 B2 | 1/2010 | Olson et al. | |
| 7,641,095 B2 | 1/2010 | Viola | |
| 7,644,848 B2 | 1/2010 | Swayze et al. | |
| 7,648,055 B2 | 1/2010 | Marczyk | |
| 7,651,017 B2 | 1/2010 | Ortiz et al. | |
| 7,654,431 B2 | 2/2010 | Hueil et al. | |
| 7,658,311 B2 | 2/2010 | Boudreaux | |
| 7,658,312 B2 | 2/2010 | Vidal et al. | |
| 7,665,646 B2 | 2/2010 | Prommersberger | |
| 7,665,647 B2 | 2/2010 | Shelton, IV et al. | |
| 7,669,746 B2 | 3/2010 | Shelton, IV | |
| 7,670,334 B2 | 3/2010 | Hueil et al. | |
| 7,673,780 B2 | 3/2010 | Shelton, IV et al. | |
| 7,673,781 B2 | 3/2010 | Swayze et al. | |
| 7,673,782 B2 | 3/2010 | Hess et al. | |
| 7,673,783 B2 | 3/2010 | Morgan et al. | |
| 7,678,121 B1 | 3/2010 | Knodel | |
| 7,681,772 B2 | 3/2010 | Green et al. | |
| 7,682,367 B2 | 3/2010 | Shah et al. | |
| 7,682,368 B1 | 3/2010 | Bombard et al. | |
| 7,690,547 B2 | 4/2010 | Racenet et al. | |
| 7,694,865 B2 | 4/2010 | Scirica | |
| 7,699,205 B2 | 4/2010 | Ivanko | |
| 7,703,653 B2 | 4/2010 | Shah et al. | |
| 7,721,931 B2 | 5/2010 | Shelton, IV et al. | |
| 7,721,933 B2 | 5/2010 | Ehrenfels et al. | |
| 7,721,935 B2 | 5/2010 | Racenet et al. | |
| 7,726,537 B2 | 6/2010 | Olson et al. | |
| 7,726,538 B2 | 6/2010 | Holsten et al. | |
| 7,726,539 B2 | 6/2010 | Holsten et al. | |
| 7,731,072 B2 | 6/2010 | Timm et al. | |
| 7,735,703 B2 | 6/2010 | Morgan et al. | |
| 7,740,159 B2 | 6/2010 | Shelton, IV et al. | |
| 7,740,160 B2 | 6/2010 | Viola | |
| 7,743,960 B2 | 6/2010 | Whitman et al. | |
| 7,744,628 B2 | 6/2010 | Viola | |
| 7,753,245 B2 | 7/2010 | Boudreaux et al. | |
| 7,753,248 B2 | 7/2010 | Viola | |
| 7,757,924 B2 | 7/2010 | Gerbi et al. | |
| 7,757,925 B2 | 7/2010 | Viola et al. | |
| 7,762,445 B2 | 7/2010 | Heinrich et al. | |
| 7,766,209 B2 | 8/2010 | Baxter, III et al. | |
| 7,766,210 B2 | 8/2010 | Shelton, IV et al. | |
| 7,766,924 B1 | 8/2010 | Bombard et al. | |
| 7,766,928 B2 | 8/2010 | Ezzat et al. | |
| 7,770,774 B2 | 8/2010 | Mastri et al. | |
| 7,770,775 B2 | 8/2010 | Shelton, IV et al. | |
| 7,776,060 B2 | 8/2010 | Mooradian et al. | |
| 7,780,055 B2 | 8/2010 | Scirica et al. | |
| 7,784,662 B2 | 8/2010 | Wales et al. | |
| 7,789,283 B2 | 9/2010 | Shah | |
| 7,789,889 B2 | 9/2010 | Zubik et al. | |
| 7,793,812 B2 | 9/2010 | Moore et al. | |
| 7,793,814 B2 | 9/2010 | Racenet et al. | |
| 7,794,475 B2 | 9/2010 | Hess et al. | |
| 7,798,385 B2 | 9/2010 | Boyden et al. | |
| 7,798,386 B2 | 9/2010 | Schall et al. | |
| 7,799,039 B2 | 9/2010 | Shelton, IV et al. | |
| 7,799,042 B2 | 9/2010 | Williamson, IV et al. | |
| 7,810,690 B2 | 10/2010 | Bilotti et al. | |
| 7,810,692 B2 | 10/2010 | Hall et al. | |
| 7,810,693 B2 | 10/2010 | Broehl et al. | |
| 7,815,090 B2 | 10/2010 | Marczyk | |
| 7,815,091 B2 | 10/2010 | Marczyk | |
| 7,815,092 B2 | 10/2010 | Whitman et al. | |
| 7,819,296 B2 | 10/2010 | Hueil et al. | |
| 7,819,297 B2 | 10/2010 | Doll et al. | |
| 7,819,298 B2 | 10/2010 | Hall et al. | |
| 7,819,299 B2 | 10/2010 | Shelton, IV et al. | |
| 7,819,896 B2 | 10/2010 | Racenet | |
| 7,823,760 B2 | 11/2010 | Zemlok et al. | |
| 7,823,761 B2 | 11/2010 | Boyden et al. | |
| 7,824,426 B2 | 11/2010 | Racenet et al. | |
| 7,828,186 B2 | 11/2010 | Wales | |
| 7,828,187 B2 | 11/2010 | Green et al. | |
| 7,828,188 B2 | 11/2010 | Jankowski | |
| 7,828,189 B2 | 11/2010 | Holsten et al. | |
| 7,832,408 B2 | 11/2010 | Shelton, IV et al. | |
| 7,832,611 B2 | 11/2010 | Boyden et al. | |
| 7,832,612 B2 | 11/2010 | Baxter, III et al. | |
| 7,834,630 B2 | 11/2010 | Damadian et al. | |
| 7,837,079 B2 | 11/2010 | Holsten et al. | |
| 7,837,081 B2 | 11/2010 | Holsten et al. | |
| 7,841,503 B2 | 11/2010 | Sonnenschein et al. | |
| 7,845,533 B2 | 12/2010 | Marczyk et al. | |
| 7,845,534 B2 | 12/2010 | Viola et al. | |
| 7,845,535 B2 | 12/2010 | Scircia | |
| 7,845,537 B2 | 12/2010 | Shelton, IV et al. | |
| 7,845,538 B2 | 12/2010 | Whitman | |
| 7,850,703 B2 | 12/2010 | Bombard et al. | |
| 7,857,183 B2 | 12/2010 | Shelton, IV | |
| 7,857,184 B2 | 12/2010 | Viola | |
| 7,857,185 B2 | 12/2010 | Swayze et al. | |
| 7,857,186 B2 | 12/2010 | Baxter, III et al. | |
| 7,861,906 B2 | 1/2011 | Doll et al. | |
| 7,861,907 B2 | 1/2011 | Green et al. | |
| 7,866,524 B2 | 1/2011 | Krehel | |
| 7,866,525 B2 | 1/2011 | Scirica | |
| 7,866,526 B2 | 1/2011 | Green et al. | |
| 7,866,527 B2 | 1/2011 | Hall et al. | |
| 7,866,528 B2 | 1/2011 | Olson et al. | |
| 7,870,989 B2 | 1/2011 | Viola et al. | |
| 7,886,952 B2 | 2/2011 | Scirica et al. | |
| 7,891,532 B2 | 2/2011 | Mastri et al. | |
| 7,891,533 B2 | 2/2011 | Green et al. | |
| 7,891,534 B2 | 2/2011 | Wenchell et al. | |
| 7,896,214 B2 | 3/2011 | Farascioni | |
| 7,900,805 B2 | 3/2011 | Shelton, IV et al. | |
| 7,901,416 B2 | 3/2011 | Nolan et al. | |
| 7,905,380 B2 | 3/2011 | Shelton, IV et al. | |
| 7,905,381 B2 | 3/2011 | Baxter, III et al. | |
| 7,909,039 B2 | 3/2011 | Hur | |
| 7,909,220 B2 | 3/2011 | Viola | |
| 7,909,221 B2 | 3/2011 | Viola et al. | |
| 7,909,224 B2 | 3/2011 | Prommersberger | |
| 7,913,891 B2 | 3/2011 | Doll et al. | |
| 7,913,893 B2 | 3/2011 | Mastri et al. | |
| 7,914,543 B2 | 3/2011 | Roth et al. | |
| 7,918,230 B2 | 4/2011 | Whitman et al. | |
| 7,922,061 B2 | 4/2011 | Shelton, IV et al. | |
| 7,922,063 B2 | 4/2011 | Zemlok et al. | |
| 7,922,064 B2 | 4/2011 | Boyden et al. | |
| 7,926,691 B2 | 4/2011 | Viola et al. | |
| 7,926,692 B2 | 4/2011 | Racenet et al. | |
| 7,934,628 B2 | 5/2011 | Wenchell et al. | |

(56) References Cited

U.S. PATENT DOCUMENTS

| | | |
|---|---|---|
| 7,934,630 B2 | 5/2011 | Shelton, IV et al. |
| 7,934,631 B2 | 5/2011 | Balbierz et al. |
| 7,942,300 B2 | 5/2011 | Rethy et al. |
| 7,942,303 B2 | 5/2011 | Shah |
| 7,950,560 B2 | 5/2011 | Zemlok et al. |
| 7,950,561 B2 | 5/2011 | Aranyi |
| 7,950,562 B2 | 5/2011 | Beardsley et al. |
| 7,954,682 B2 | 6/2011 | Giordano et al. |
| 7,954,683 B1 | 6/2011 | Knodel et al. |
| 7,954,684 B2 | 6/2011 | Boudreaux |
| 7,954,685 B2 | 6/2011 | Viola |
| 7,954,686 B2 | 6/2011 | Baxter, III et al. |
| 7,954,687 B2 | 6/2011 | Zemlok et al. |
| 7,959,051 B2 | 6/2011 | Smith et al. |
| 7,963,431 B2 | 6/2011 | Scirica |
| 7,963,432 B2 | 6/2011 | Knodel et al. |
| 7,963,433 B2 | 6/2011 | Whitman et al. |
| 7,967,178 B2 | 6/2011 | Scirica et al. |
| 7,967,179 B2 | 6/2011 | Olson et al. |
| 7,967,180 B2 | 6/2011 | Scirica |
| 7,975,894 B2 | 7/2011 | Boyden et al. |
| 7,980,443 B2 | 7/2011 | Scheib et al. |
| 7,988,026 B2 | 8/2011 | Knodel et al. |
| 7,988,027 B2 | 8/2011 | Olson et al. |
| 7,988,028 B2 | 8/2011 | Farascioni et al. |
| 7,992,758 B2 | 8/2011 | Whitman et al. |
| 7,997,468 B2 | 8/2011 | Farascioni |
| 7,997,469 B2 | 8/2011 | Olson et al. |
| 8,002,795 B2 | 8/2011 | Beetel |
| 8,006,885 B2 | 8/2011 | Marczyk |
| 8,006,887 B2 | 8/2011 | Marczyk |
| 8,007,505 B2 | 8/2011 | Weller et al. |
| 8,007,513 B2 | 8/2011 | Nalagatla et al. |
| 8,011,550 B2 | 9/2011 | Aranyi et al. |
| 8,011,551 B2 | 9/2011 | Marczyk et al. |
| 8,011,552 B2 | 9/2011 | Ivanko |
| 8,011,553 B2 | 9/2011 | Mastri et al. |
| 8,011,555 B2 | 9/2011 | Tarinelli et al. |
| 8,012,170 B2 | 9/2011 | Whitman et al. |
| 8,015,976 B2 | 9/2011 | Shah |
| 8,016,177 B2 | 9/2011 | Bettuchi et al. |
| 8,016,178 B2 | 9/2011 | Olson et al. |
| 8,020,742 B2 | 9/2011 | Marczyk |
| 8,020,743 B2 | 9/2011 | Shelton, IV |
| 8,028,882 B2 | 10/2011 | Viola |
| 8,028,883 B2 | 10/2011 | Stopek |
| 8,028,884 B2 | 10/2011 | Sniffin et al. |
| 8,033,438 B2 | 10/2011 | Scirica |
| 8,033,440 B2 | 10/2011 | Wenchell et al. |
| 8,033,441 B2 | 10/2011 | Marczyk |
| 8,033,442 B2 | 10/2011 | Racenet et al. |
| 8,034,077 B2 | 10/2011 | Smith et al. |
| 8,038,044 B2 | 10/2011 | Viola |
| 8,038,045 B2 | 10/2011 | Bettuchi et al. |
| 8,052,024 B2 | 11/2011 | Viola et al. |
| 8,056,787 B2 | 11/2011 | Boudreaux et al. |
| 8,056,788 B2 | 11/2011 | Mastri et al. |
| 8,056,791 B2 | 11/2011 | Whitman |
| 8,061,577 B2 | 11/2011 | Racenet et al. |
| 8,066,166 B2 | 11/2011 | Demmy et al. |
| 8,070,033 B2 | 12/2011 | Milliman et al. |
| 8,070,034 B1 | 12/2011 | Knodel |
| 8,070,035 B2 | 12/2011 | Holsten et al. |
| 8,074,858 B2 | 12/2011 | Marczyk |
| 8,074,859 B2 | 12/2011 | Kostrzewski |
| 8,074,862 B2 | 12/2011 | Shah |
| 8,083,118 B2 | 12/2011 | Milliman et al. |
| 8,083,119 B2 | 12/2011 | Prommersberger |
| 8,083,120 B2 | 12/2011 | Shelton, IV et al. |
| 8,087,563 B2 | 1/2012 | Milliman et al. |
| 8,091,753 B2 | 1/2012 | Viola |
| 8,091,754 B2 | 1/2012 | Ehrenfels et al. |
| 8,091,756 B2 | 1/2012 | Viola |
| 8,092,493 B2 | 1/2012 | Marczyk |
| 8,096,459 B2 * | 1/2012 | Ortiz ................ A61B 17/072 227/176.1 |
| 8,096,460 B2 | 1/2012 | Blier et al. |
| 8,100,309 B2 | 1/2012 | Marczyk |
| 8,100,310 B2 | 1/2012 | Zemlok |
| 8,102,008 B2 | 1/2012 | Wells |
| 8,113,406 B2 | 2/2012 | Holsten et al. |
| 8,113,407 B2 | 2/2012 | Holsten et al. |
| 8,113,408 B2 | 2/2012 | Wenchell et al. |
| 8,113,409 B2 | 2/2012 | Cohen et al. |
| 8,113,410 B2 | 2/2012 | Hall et al. |
| 8,123,101 B2 | 2/2012 | Racenet et al. |
| 8,127,975 B2 | 3/2012 | Olson et al. |
| 8,127,976 B2 | 3/2012 | Scirica et al. |
| 8,132,703 B2 | 3/2012 | Milliman et al. |
| 8,132,705 B2 | 3/2012 | Viola et al. |
| 8,132,706 B2 | 3/2012 | Marczyk et al. |
| 8,136,713 B2 | 3/2012 | Hathaway et al. |
| 8,141,762 B2 | 3/2012 | Bedi et al. |
| 8,152,041 B2 | 4/2012 | Kostrzewski |
| 8,157,148 B2 | 4/2012 | Scirica |
| 8,157,150 B2 | 4/2012 | Viola et al. |
| 8,157,151 B2 | 4/2012 | Ingmanson et al. |
| 8,157,152 B2 | 4/2012 | Holsten et al. |
| 8,162,197 B2 | 4/2012 | Mastri et al. |
| 8,167,185 B2 | 5/2012 | Shelton, IV et al. |
| 8,167,186 B2 | 5/2012 | Racenet et al. |
| 8,172,121 B2 | 5/2012 | Krehel |
| 8,172,124 B2 | 5/2012 | Shelton, IV et al. |
| 8,181,837 B2 | 5/2012 | Roy |
| 8,186,555 B2 | 5/2012 | Shelton, IV et al. |
| 8,186,557 B2 | 5/2012 | Cohen et al. |
| 8,186,558 B2 | 5/2012 | Sapienza |
| 8,186,559 B1 | 5/2012 | Whitman |
| 8,186,560 B2 | 5/2012 | Hess et al. |
| 8,193,044 B2 | 6/2012 | Kenneth |
| 8,196,795 B2 | 6/2012 | Moore et al. |
| 8,196,796 B2 | 6/2012 | Shelton, IV et al. |
| 8,201,721 B2 | 6/2012 | Zemlok et al. |
| 8,205,619 B2 | 6/2012 | Shah et al. |
| 8,205,780 B2 | 6/2012 | Sorrentino et al. |
| 8,205,781 B2 | 6/2012 | Baxter, III et al. |
| 8,210,412 B2 | 7/2012 | Marczyk |
| 8,210,416 B2 | 7/2012 | Milliman et al. |
| 8,215,532 B2 | 7/2012 | Marczyk |
| 8,216,236 B2 | 7/2012 | Heinrich et al. |
| 8,220,688 B2 | 7/2012 | Laurent et al. |
| 8,220,690 B2 | 7/2012 | Hess et al. |
| 8,225,979 B2 | 7/2012 | Farascioni et al. |
| 8,231,040 B2 | 7/2012 | Zemlok et al. |
| 8,231,041 B2 | 7/2012 | Marczyk et al. |
| 8,235,272 B2 | 8/2012 | Nicholas et al. |
| 8,235,273 B2 | 8/2012 | Olson et al. |
| 8,235,274 B2 | 8/2012 | Cappola |
| 8,236,010 B2 | 8/2012 | Ortiz et al. |
| 8,240,536 B2 | 8/2012 | Marczyk |
| 8,240,537 B2 | 8/2012 | Marczyk |
| 8,241,322 B2 | 8/2012 | Whitman et al. |
| 8,245,897 B2 | 8/2012 | Tzakis et al. |
| 8,245,898 B2 | 8/2012 | Smith et al. |
| 8,245,899 B2 | 8/2012 | Swensgard et al. |
| 8,245,931 B2 | 8/2012 | Shigeta |
| 8,252,009 B2 | 8/2012 | Weller et al. |
| 8,256,653 B2 | 9/2012 | Farascioni |
| 8,256,654 B2 | 9/2012 | Bettuchi et al. |
| 8,256,655 B2 | 9/2012 | Sniffin et al. |
| 8,256,656 B2 | 9/2012 | Milliman et al. |
| 8,267,300 B2 | 9/2012 | Boudreaux |
| 8,272,551 B2 | 9/2012 | Knodel et al. |
| 8,272,553 B2 | 9/2012 | Mastri et al. |
| 8,272,554 B2 | 9/2012 | Whitman et al. |
| 8,276,594 B2 | 10/2012 | Shah |
| 8,276,801 B2 | 10/2012 | Zemlok et al. |
| 8,281,973 B2 | 10/2012 | Wenchell et al. |
| 8,286,847 B2 | 10/2012 | Taylor |
| 8,286,848 B2 | 10/2012 | Wenchell et al. |
| 8,286,850 B2 | 10/2012 | Viola |
| 8,292,146 B2 | 10/2012 | Holsten et al. |
| 8,292,147 B2 | 10/2012 | Viola |

(56) References Cited

U.S. PATENT DOCUMENTS

| | | |
|---|---|---|
| 8,292,148 B2 | 10/2012 | Viola |
| 8,292,149 B2 | 10/2012 | Ivanko |
| 8,292,150 B2 | 10/2012 | Bryant |
| 8,292,151 B2 | 10/2012 | Viola |
| 8,292,152 B2 | 10/2012 | Milliman et al. |
| 8,292,153 B2 | 10/2012 | Jankowski |
| 8,292,154 B2 | 10/2012 | Marczyk |
| 8,292,155 B2 | 10/2012 | Shelton, IV et al. |
| 8,292,156 B2 | 10/2012 | Kostrzewski |
| 8,292,158 B2 | 10/2012 | Sapienza |
| 8,308,040 B2 | 11/2012 | Huang et al. |
| 8,308,041 B2 | 11/2012 | Kostrzewski |
| 8,308,042 B2 | 11/2012 | Aranyi |
| 8,308,043 B2 | 11/2012 | Bindra et al. |
| 8,308,044 B2 | 11/2012 | Viola |
| 8,308,046 B2 | 11/2012 | Prommersberger |
| 8,308,757 B2 | 11/2012 | Hillstead et al. |
| 8,317,070 B2 | 11/2012 | Hueil et al. |
| 8,317,071 B1 | 11/2012 | Knodel |
| 8,322,455 B2 | 12/2012 | Shelton, IV et al. |
| 8,322,589 B2 | 12/2012 | Boudreaux |
| 8,328,061 B2 | 12/2012 | Kasvikis |
| 8,328,065 B2 | 12/2012 | Shah |
| 8,333,313 B2 | 12/2012 | Boudreaux et al. |
| 8,336,751 B2 | 12/2012 | Scirica |
| 8,336,753 B2 | 12/2012 | Olson et al. |
| 8,336,754 B2 | 12/2012 | Cappola et al. |
| 8,342,377 B2 | 1/2013 | Milliman et al. |
| 8,342,378 B2 | 1/2013 | Marczyk et al. |
| 8,342,379 B2 | 1/2013 | Whitman et al. |
| 8,342,380 B2 | 1/2013 | Viola |
| 8,348,123 B2 | 1/2013 | Scirica et al. |
| 8,348,124 B2 | 1/2013 | Scirica |
| 8,348,125 B2 | 1/2013 | Viola et al. |
| 8,348,126 B2 | 1/2013 | Olson et al. |
| 8,348,127 B2 | 1/2013 | Marczyk |
| 8,348,129 B2 | 1/2013 | Bedi et al. |
| 8,348,130 B2 | 1/2013 | Shah et al. |
| 8,348,131 B2 | 1/2013 | Omaits et al. |
| 8,353,437 B2 | 1/2013 | Boudreaux |
| 8,353,440 B2 | 1/2013 | Whitman et al. |
| 8,356,740 B1 | 1/2013 | Knodel |
| 8,357,174 B2 | 1/2013 | Roth et al. |
| 8,360,294 B2 | 1/2013 | Scirica |
| 8,360,297 B2 | 1/2013 | Shelton, IV et al. |
| 8,360,298 B2 | 1/2013 | Farascioni et al. |
| 8,360,299 B2 | 1/2013 | Zemlok et al. |
| 8,365,971 B1 | 2/2013 | Knodel |
| 8,365,972 B2 | 2/2013 | Aranyi et al. |
| 8,365,973 B1 | 2/2013 | White et al. |
| 8,365,976 B2 | 2/2013 | Hess et al. |
| 8,371,491 B2 | 2/2013 | Huitema et al. |
| 8,371,492 B2 | 2/2013 | Aranyi et al. |
| 8,371,493 B2 | 2/2013 | Aranyi et al. |
| 8,381,828 B2 | 2/2013 | Whitman et al. |
| 8,381,961 B2 | 2/2013 | Holsten et al. |
| 8,387,848 B2 | 3/2013 | Johnson et al. |
| 8,387,849 B2 | 3/2013 | Buesseler et al. |
| 8,387,850 B2 | 3/2013 | Hathaway et al. |
| 8,388,652 B2 | 3/2013 | Viola |
| 8,393,513 B2 | 3/2013 | Jankowski |
| 8,393,514 B2 | 3/2013 | Shelton, IV et al. |
| 8,393,516 B2 | 3/2013 | Kostrzewski |
| 8,397,971 B2 | 3/2013 | Yates et al. |
| 8,397,972 B2 | 3/2013 | Kostrzewski |
| 8,403,195 B2 | 3/2013 | Beardsley et al. |
| 8,403,196 B2 | 3/2013 | Beardsley et al. |
| 8,403,197 B2 | 3/2013 | Vidal et al. |
| 8,403,198 B2 | 3/2013 | Sorrentino et al. |
| 8,403,956 B1 | 3/2013 | Thompson et al. |
| 8,408,439 B2 | 4/2013 | Huang et al. |
| 8,408,440 B2 | 4/2013 | Olson et al. |
| 8,408,442 B2 | 4/2013 | Racenet et al. |
| 8,413,868 B2 | 4/2013 | Cappola |
| 8,413,869 B2 | 4/2013 | Heinrich |
| 8,413,871 B2 | 4/2013 | Racenet et al. |
| 8,418,904 B2 | 4/2013 | Wenchell et al. |
| 8,418,905 B2 | 4/2013 | Milliman |
| 8,418,906 B2 | 4/2013 | Farascioni et al. |
| 8,418,907 B2 | 4/2013 | Johnson et al. |
| 8,418,908 B1 | 4/2013 | Beardsley |
| 8,419,768 B2 | 4/2013 | Marczyk |
| 8,424,735 B2 | 4/2013 | Viola et al. |
| 8,424,736 B2 | 4/2013 | Scirica et al. |
| 8,424,737 B2 | 4/2013 | Scirica |
| 8,424,739 B2 | 4/2013 | Racenet et al. |
| 8,424,740 B2 | 4/2013 | Shelton, IV et al. |
| 8,439,244 B2 | 5/2013 | Holcomb et al. |
| 8,439,245 B2 | 5/2013 | Knodel et al. |
| 8,439,246 B1 | 5/2013 | Knodel |
| 8,444,036 B2 | 5/2013 | Shelton, IV |
| 8,444,037 B2 | 5/2013 | Nicholas et al. |
| 8,444,038 B2 | 5/2013 | Farascioni et al. |
| 8,448,832 B2 | 5/2013 | Viola et al. |
| 8,453,652 B2 | 6/2013 | Stopek |
| 8,453,905 B2 | 6/2013 | Holcomb et al. |
| 8,453,906 B2 | 6/2013 | Huang et al. |
| 8,453,907 B2 | 6/2013 | Laurent et al. |
| 8,453,908 B2 | 6/2013 | Bedi et al. |
| 8,453,909 B2 | 6/2013 | Olson et al. |
| 8,453,910 B2 | 6/2013 | Bettuchi et al. |
| 8,453,912 B2 | 6/2013 | Mastri et al. |
| 8,453,913 B2 | 6/2013 | Milliman |
| 8,453,914 B2 | 6/2013 | Laurent et al. |
| 8,454,628 B2 | 6/2013 | Smith et al. |
| 8,459,520 B2 | 6/2013 | Giordano et al. |
| 8,459,521 B2 | 6/2013 | Zemlok et al. |
| 8,459,522 B2 | 6/2013 | Marczyk |
| 8,459,523 B2 | 6/2013 | Whitman |
| 8,459,524 B2 | 6/2013 | Pribanic et al. |
| 8,459,525 B2 | 6/2013 | Yates et al. |
| 8,464,922 B2 | 6/2013 | Marczyk |
| 8,464,923 B2 | 6/2013 | Shelton, IV |
| 8,469,252 B2 | 6/2013 | Holcomb et al. |
| 8,469,254 B2 | 6/2013 | Czemik et al. |
| 8,474,677 B2 | 7/2013 | Woodard, Jr. et al. |
| 8,479,967 B2 | 7/2013 | Marczyk |
| 8,479,968 B2 | 7/2013 | Hodgkinson et al. |
| 8,479,969 B2 | 7/2013 | Shelton, IV |
| 8,485,412 B2 | 7/2013 | Shelton, IV et al. |
| 8,490,852 B2 | 7/2013 | Viola |
| 8,496,152 B2 | 7/2013 | Viola |
| 8,496,154 B2 | 7/2013 | Marczyk et al. |
| 8,496,156 B2 | 7/2013 | Sniffin et al. |
| 8,496,683 B2 | 7/2013 | Prommersberger et al. |
| 8,499,993 B2 | 8/2013 | Shelton, IV et al. |
| 8,505,799 B2 | 8/2013 | Viola et al. |
| 8,505,802 B2 | 8/2013 | Viola et al. |
| 8,511,575 B2 | 8/2013 | Cok |
| 8,512,359 B2 | 8/2013 | Whitman et al. |
| 8,512,402 B2 | 8/2013 | Marczyk et al. |
| 8,517,240 B1 | 8/2013 | Mata et al. |
| 8,517,241 B2 | 8/2013 | Nicholas et al. |
| 8,517,243 B2 | 8/2013 | Giordano et al. |
| 8,517,244 B2 | 8/2013 | Shelton, IV et al. |
| 8,523,041 B2 | 9/2013 | Ishitsuki et al. |
| 8,523,042 B2 | 9/2013 | Masiakos et al. |
| 8,523,043 B2 | 9/2013 | Ullrich et al. |
| 8,534,528 B2 | 9/2013 | Shelton, IV |
| 8,540,128 B2 | 9/2013 | Shelton, IV et al. |
| 8,540,129 B2 | 9/2013 | Baxter, III et al. |
| 8,540,130 B2 | 9/2013 | Moore et al. |
| 8,540,131 B2 | 9/2013 | Swayze |
| 8,540,733 B2 | 9/2013 | Whitman et al. |
| 8,544,711 B2 | 10/2013 | Ma et al. |
| 8,550,325 B2 | 10/2013 | Cohen et al. |
| 8,556,151 B2 | 10/2013 | Viola |
| 8,561,870 B2 | 10/2013 | Baxter, III et al. |
| 8,561,873 B2 | 10/2013 | Ingmanson et al. |
| 8,561,874 B2 | 10/2013 | Scirica |
| 8,567,656 B2 | 10/2013 | Shelton, IV et al. |
| 8,573,461 B2 | 11/2013 | Shelton, IV et al. |
| 8,573,463 B2 | 11/2013 | Scirica et al. |
| 8,573,465 B2 | 11/2013 | Shelton, IV |

(56) References Cited

U.S. PATENT DOCUMENTS

| | | |
|---|---|---|
| 8,579,176 B2 | 11/2013 | Smith et al. |
| 8,579,177 B2 | 11/2013 | Beetel |
| 8,584,919 B2 | 11/2013 | Hueil et al. |
| 8,584,920 B2 | 11/2013 | Hodgkinson |
| 8,590,761 B2 * | 11/2013 | Gerbi ............... A61B 17/29 227/175.1 |
| 8,590,762 B2 | 11/2013 | Hess et al. |
| 8,596,515 B2 | 12/2013 | Okoniewski |
| 8,602,288 B2 | 12/2013 | Shelton, IV et al. |
| 8,608,045 B2 | 12/2013 | Smith et al. |
| 8,608,046 B2 | 12/2013 | Laurent et al. |
| 8,608,047 B2 | 12/2013 | Holsten et al. |
| 8,613,383 B2 | 12/2013 | Beckman et al. |
| 8,613,384 B2 | 12/2013 | Pastorelli et al. |
| 8,616,427 B2 | 12/2013 | Viola |
| 8,616,430 B2 | 12/2013 | (Prommersberger) Stopek |
| 8,627,994 B2 | 1/2014 | Zemlok et al. |
| 8,628,544 B2 | 1/2014 | Farascioni |
| 8,631,988 B2 | 1/2014 | Viola |
| 8,631,989 B2 | 1/2014 | Aranyi et al. |
| 8,631,991 B2 | 1/2014 | Cropper et al. |
| 8,632,525 B2 | 1/2014 | Kerr et al. |
| 8,632,535 B2 | 1/2014 | Shelton, IV et al. |
| 8,636,187 B2 | 1/2014 | Hueil et al. |
| 8,636,190 B2 | 1/2014 | Zemlok et al. |
| 8,636,192 B2 | 1/2014 | Farascioni et al. |
| 8,636,762 B2 | 1/2014 | Whitman et al. |
| 8,636,766 B2 | 1/2014 | Milliman et al. |
| 8,640,940 B2 | 2/2014 | Ohdaira |
| 8,657,174 B2 | 2/2014 | Yates et al. |
| 8,657,177 B2 | 2/2014 | Scirica et al. |
| 8,657,178 B2 | 2/2014 | Hueil et al. |
| 8,662,371 B2 | 3/2014 | Viola |
| 8,668,129 B2 | 3/2014 | Olson |
| 8,672,206 B2 | 3/2014 | Aranyi et al. |
| 8,672,208 B2 | 3/2014 | Hess et al. |
| 8,672,209 B2 | 3/2014 | Crainich |
| 8,678,263 B2 | 3/2014 | Viola |
| 8,678,990 B2 | 3/2014 | Wazer et al. |
| 8,679,155 B2 | 3/2014 | Knodel et al. |
| 8,684,247 B2 | 4/2014 | Scirica et al. |
| 8,684,249 B2 | 4/2014 | Racenet et al. |
| 8,684,253 B2 | 4/2014 | Giordano et al. |
| 8,690,039 B2 | 4/2014 | Beardsley et al. |
| 8,695,865 B2 | 4/2014 | Smith et al. |
| 8,695,866 B2 | 4/2014 | Leimbach et al. |
| 8,701,958 B2 | 4/2014 | Shelton, IV et al. |
| 8,701,959 B2 | 4/2014 | Shah |
| 8,701,961 B2 | 4/2014 | Ivanko |
| 8,708,213 B2 | 4/2014 | Shelton, IV et al. |
| 8,714,429 B2 | 5/2014 | Demmy |
| 8,715,277 B2 | 5/2014 | Weizman |
| 8,720,766 B2 | 5/2014 | Hess et al. |
| 8,721,630 B2 | 5/2014 | Ortiz et al. |
| 8,727,197 B2 | 5/2014 | Hess et al. |
| 8,727,200 B2 | 5/2014 | Roy |
| 8,733,612 B2 | 5/2014 | Ma |
| 8,740,034 B2 | 6/2014 | Morgan et al. |
| 8,740,039 B2 | 6/2014 | Farascioni |
| 8,746,529 B2 | 6/2014 | Shelton, IV et al. |
| 8,746,530 B2 | 6/2014 | Giordano et al. |
| 8,746,535 B2 | 6/2014 | Shelton, IV et al. |
| 8,752,748 B2 | 6/2014 | Whitman et al. |
| 8,752,749 B2 | 6/2014 | Moore et al. |
| 8,757,465 B2 | 6/2014 | Woodard, Jr. et al. |
| 8,758,391 B2 | 6/2014 | Swayze et al. |
| 8,763,877 B2 | 7/2014 | Schall et al. |
| 8,763,879 B2 | 7/2014 | Shelton, IV et al. |
| 8,770,458 B2 | 7/2014 | Scirica |
| 8,777,082 B2 | 7/2014 | Scirica |
| 8,783,541 B2 | 7/2014 | Shelton, IV et al. |
| 8,783,542 B2 | 7/2014 | Riestenberg et al. |
| 8,789,737 B2 | 7/2014 | Hodgkinson et al. |
| 8,789,738 B2 | 7/2014 | Knodel et al. |
| 8,789,739 B2 | 7/2014 | Swensgard |
| 8,800,838 B2 | 8/2014 | Shelton, IV |
| 8,800,840 B2 | 8/2014 | Jankowski |
| 8,800,841 B2 | 8/2014 | Ellerhorst et al. |
| 8,808,311 B2 | 8/2014 | Heinrich et al. |
| 8,814,024 B2 | 8/2014 | Woodard, Jr. et al. |
| 8,814,025 B2 | 8/2014 | Miller et al. |
| 8,820,603 B2 | 9/2014 | Shelton, IV et al. |
| 8,820,605 B2 | 9/2014 | Shelton, IV |
| 8,820,607 B2 | 9/2014 | Marczyk |
| 8,827,133 B2 | 9/2014 | Shelton, IV et al. |
| 8,827,134 B2 | 9/2014 | Viola et al. |
| 8,833,631 B2 | 9/2014 | Munro, III et al. |
| 8,833,632 B2 | 9/2014 | Swensgard |
| 8,840,003 B2 | 9/2014 | Morgan et al. |
| 8,840,603 B2 | 9/2014 | Shelton, IV et al. |
| 8,844,788 B2 | 9/2014 | Knodel |
| 8,851,354 B2 | 10/2014 | Swensgard et al. |
| 8,851,355 B2 | 10/2014 | Aranyi et al. |
| 8,857,693 B2 | 10/2014 | Schuckmann et al. |
| 8,864,007 B2 | 10/2014 | Widenhouse et al. |
| 8,864,009 B2 | 10/2014 | Shelton, IV et al. |
| 8,875,971 B2 | 11/2014 | Hall et al. |
| 8,875,972 B2 | 11/2014 | Weisenburgh, II et al. |
| 8,893,949 B2 | 11/2014 | Shelton, IV et al. |
| 8,893,950 B2 | 11/2014 | Marczyk |
| 8,899,461 B2 | 12/2014 | Farascioni |
| 8,899,463 B2 | 12/2014 | Schall et al. |
| 8,899,464 B2 | 12/2014 | Hueil et al. |
| 8,900,616 B2 | 12/2014 | Belcheva et al. |
| 8,920,435 B2 | 12/2014 | Smith et al. |
| 8,925,782 B2 | 1/2015 | Shelton, IV |
| 8,926,598 B2 | 1/2015 | Mollere et al. |
| 8,931,682 B2 | 1/2015 | Timm et al. |
| 8,931,693 B1 | 1/2015 | Kumar et al. |
| 8,955,732 B2 | 2/2015 | Zemlok et al. |
| 8,958,429 B2 | 2/2015 | Shukla et al. |
| 8,960,517 B2 | 2/2015 | Lee |
| 8,967,443 B2 | 3/2015 | McCuen |
| 8,967,446 B2 | 3/2015 | Beardsley et al. |
| 8,973,803 B2 | 3/2015 | Hall et al. |
| 8,978,954 B2 | 3/2015 | Shelton, IV et al. |
| 8,978,956 B2 | 3/2015 | Schall et al. |
| 8,998,060 B2 | 4/2015 | Bruewer et al. |
| 9,005,230 B2 | 4/2015 | Yates et al. |
| 9,010,607 B2 | 4/2015 | Kostrzewski |
| 9,016,539 B2 | 4/2015 | Kostrzewski et al. |
| 9,016,541 B2 | 4/2015 | Viola et al. |
| 9,016,542 B2 | 4/2015 | Shelton, IV et al. |
| 9,016,546 B2 | 4/2015 | Demmy et al. |
| 9,022,271 B2 | 5/2015 | Scirica |
| 9,027,817 B2 | 5/2015 | Milliman et al. |
| 9,033,203 B2 | 5/2015 | Woodard, Jr. et al. |
| 9,044,228 B2 | 6/2015 | Woodard, Jr. et al. |
| 9,044,229 B2 | 6/2015 | Scheib et al. |
| 9,050,084 B2 | 6/2015 | Schmid et al. |
| 9,055,941 B2 | 6/2015 | Schmid et al. |
| 9,060,770 B2 | 6/2015 | Shelton, IV et al. |
| 9,072,535 B2 | 7/2015 | Shelton, IV et al. |
| 9,089,326 B2 | 7/2015 | Krumanaker et al. |
| 9,101,359 B2 | 8/2015 | Smith et al. |
| 9,107,663 B2 | 8/2015 | Swensgard |
| 9,107,664 B2 | 8/2015 | Marczyk |
| 9,113,862 B2 | 8/2015 | Morgan et al. |
| 9,113,864 B2 | 8/2015 | Morgan et al. |
| 9,113,870 B2 | 8/2015 | Viola |
| 9,113,872 B2 | 8/2015 | Viola |
| 9,113,880 B2 | 8/2015 | Zemlok et al. |
| 9,119,657 B2 * | 9/2015 | Shelton, IV ............ A61B 17/29 |
| 9,125,649 B2 | 9/2015 | Bruewer et al. |
| 9,138,225 B2 | 9/2015 | Huang et al. |
| 9,155,537 B2 | 10/2015 | Katre et al. |
| 9,168,050 B1 * | 10/2015 | Peine ............... A61B 17/29 |
| 9,179,912 B2 | 11/2015 | Yates et al. |
| 9,192,378 B2 | 11/2015 | Aranyi et al. |
| 9,192,379 B2 | 11/2015 | Aranyi et al. |
| 9,192,384 B2 | 11/2015 | Bettuchi |
| 9,198,644 B2 | 12/2015 | Balek et al. |
| 9,198,661 B2 | 12/2015 | Swensgard |
| 9,204,876 B2 | 12/2015 | Cappola et al. |

(56) References Cited

U.S. PATENT DOCUMENTS

| | | |
|---|---|---|
| 9,216,019 B2 | 12/2015 | Schmid et al. |
| 9,216,020 B2 | 12/2015 | Zhang et al. |
| 9,220,500 B2 | 12/2015 | Swayze et al. |
| 9,220,501 B2 | 12/2015 | Baxter, III et al. |
| 9,220,502 B2 | 12/2015 | Zemlok et al. |
| 9,232,941 B2 | 1/2016 | Mandakolathur Vasudevan et al. |
| 9,232,944 B2 | 1/2016 | Cappola et al. |
| 9,237,891 B2 | 1/2016 | Shelton, IV |
| 9,237,900 B2 * | 1/2016 | Boudreaux ............ A61B 18/00 |
| 9,254,180 B2 | 2/2016 | Huitema et al. |
| 9,265,585 B2 | 2/2016 | Wingardner et al. |
| 9,271,728 B2 | 3/2016 | Gupta et al. |
| 9,277,919 B2 | 3/2016 | Timmer et al. |
| 9,282,962 B2 | 3/2016 | Schmid et al. |
| 9,283,054 B2 | 3/2016 | Morgan et al. |
| 9,289,209 B2 | 3/2016 | Gurumurthy et al. |
| 9,289,210 B2 | 3/2016 | Baxter, III et al. |
| 9,289,225 B2 | 3/2016 | Shelton, IV et al. |
| 9,295,464 B2 | 3/2016 | Shelton, IV et al. |
| 9,295,465 B2 | 3/2016 | Farascioni |
| 9,301,752 B2 | 4/2016 | Mandakolathur Vasudevan et al. |
| 9,301,753 B2 | 4/2016 | Aldridge et al. |
| 9,301,757 B2 | 4/2016 | Williams |
| 9,307,965 B2 | 4/2016 | Ming et al. |
| 9,307,986 B2 | 4/2016 | Hall et al. |
| 9,307,989 B2 | 4/2016 | Shelton, IV et al. |
| 9,314,246 B2 | 4/2016 | Shelton, IV et al. |
| 9,320,518 B2 | 4/2016 | Henderson et al. |
| 9,320,521 B2 | 4/2016 | Shelton, IV et al. |
| 9,326,767 B2 | 5/2016 | Koch, Jr. et al. |
| 9,332,987 B2 | 5/2016 | Leimbach et al. |
| 9,345,477 B2 | 5/2016 | Anim et al. |
| 9,345,478 B2 | 5/2016 | Knodel |
| 9,345,481 B2 | 5/2016 | Hall et al. |
| 9,345,780 B2 | 5/2016 | Manoharan et al. |
| 9,351,727 B2 | 5/2016 | Leimbach et al. |
| 9,351,732 B2 | 5/2016 | Hodgkinson |
| 9,358,003 B2 | 6/2016 | Hall et al. |
| 9,364,217 B2 | 6/2016 | Kostrzewski et al. |
| 9,364,218 B2 | 6/2016 | Scirica |
| 9,364,219 B2 | 6/2016 | Olson et al. |
| 9,364,220 B2 | 6/2016 | Williams |
| 9,364,233 B2 | 6/2016 | Alexander, III et al. |
| 9,370,358 B2 | 6/2016 | Shelton, IV et al. |
| 9,370,362 B2 | 6/2016 | Petty et al. |
| 9,386,983 B2 | 7/2016 | Swensgard et al. |
| 9,386,984 B2 | 7/2016 | Aronhalt et al. |
| 9,386,988 B2 | 7/2016 | Baxter, III et al. |
| 9,393,018 B2 | 7/2016 | Wang et al. |
| 9,398,911 B2 | 7/2016 | Auld |
| 9,402,604 B2 | 8/2016 | Williams et al. |
| 9,421,014 B2 | 8/2016 | Ingmanson et al. |
| 9,433,419 B2 | 9/2016 | Gonzalez et al. |
| 9,433,420 B2 | 9/2016 | Hodgkinson |
| 9,445,810 B2 | 9/2016 | Cappola |
| 9,445,813 B2 | 9/2016 | Shelton, IV et al. |
| 9,451,959 B2 | 9/2016 | Patankar et al. |
| 9,468,438 B2 | 10/2016 | Baber et al. |
| 9,468,439 B2 | 10/2016 | Cappola et al. |
| 9,480,476 B2 | 11/2016 | Aldridge et al. |
| 9,480,492 B2 | 11/2016 | Aranyi et al. |
| 9,492,171 B2 | 11/2016 | Patenaude |
| 9,498,212 B2 | 11/2016 | Racenet et al. |
| 9,510,827 B2 | 12/2016 | Kostrzewski |
| 9,517,065 B2 | 12/2016 | Simms et al. |
| 9,517,066 B2 | 12/2016 | Racenet et al. |
| 9,539,007 B2 | 1/2017 | Dhakad et al. |
| 9,549,735 B2 | 1/2017 | Shelton, IV et al. |
| 9,629,621 B2 * | 4/2017 | Hessler ................ A61B 17/115 |
| 2004/0108357 A1 | 6/2004 | Milliman et al. |
| 2004/0199180 A1 | 10/2004 | Knodel et al. |
| 2004/0199181 A1 | 10/2004 | Knodel et al. |
| 2004/0243151 A1 | 12/2004 | Demmy et al. |
| 2004/0267310 A1 | 12/2004 | Racenet et al. |
| 2005/0006429 A1 | 1/2005 | Wales et al. |
| 2005/0216055 A1 | 9/2005 | Scirica et al. |
| 2006/0049229 A1 | 3/2006 | Milliman et al. |
| 2006/0180634 A1 | 8/2006 | Shelton et al. |
| 2006/0289602 A1 | 12/2006 | Wales et al. |
| 2007/0073341 A1 | 3/2007 | Smith et al. |
| 2007/0084897 A1 | 4/2007 | Shelton et al. |
| 2007/0102472 A1 | 5/2007 | Shelton |
| 2007/0106317 A1 | 5/2007 | Shelton et al. |
| 2007/0119901 A1 | 5/2007 | Ehrenfels et al. |
| 2007/0145096 A1 | 6/2007 | Viola et al. |
| 2007/0170225 A1 | 7/2007 | Shelton et al. |
| 2007/0175950 A1 | 8/2007 | Shelton et al. |
| 2007/0175951 A1 | 8/2007 | Shelton et al. |
| 2007/0175955 A1 | 8/2007 | Shelton et al. |
| 2007/0179528 A1 | 8/2007 | Soltz et al. |
| 2007/0194079 A1 | 8/2007 | Hueil et al. |
| 2007/0194082 A1 | 8/2007 | Morgan et al. |
| 2008/0029570 A1 | 2/2008 | Shelton et al. |
| 2008/0029573 A1 | 2/2008 | Shelton et al. |
| 2008/0029574 A1 | 2/2008 | Shelton et al. |
| 2008/0029575 A1 | 2/2008 | Shelton et al. |
| 2008/0078802 A1 | 4/2008 | Hess et al. |
| 2008/0110961 A1 | 5/2008 | Voegele et al. |
| 2008/0169328 A1 | 7/2008 | Shelton |
| 2008/0169332 A1 | 7/2008 | Shelton et al. |
| 2008/0169333 A1 | 7/2008 | Shelton et al. |
| 2008/0287987 A1 | 11/2008 | Boyden et al. |
| 2008/0296346 A1 | 12/2008 | Shelton, IV et al. |
| 2008/0308602 A1 | 12/2008 | Timm et al. |
| 2008/0308603 A1 | 12/2008 | Shelton et al. |
| 2009/0001121 A1 | 1/2009 | Hess et al. |
| 2009/0001130 A1 | 1/2009 | Hess et al. |
| 2009/0090763 A1 | 4/2009 | Zemlok et al. |
| 2009/0090766 A1 | 4/2009 | Knodel |
| 2009/0242610 A1 | 10/2009 | Shelton, IV et al. |
| 2009/0255974 A1 | 10/2009 | Viola |
| 2009/0277944 A9 * | 11/2009 | Dalessandro .... A61B 17/07207 227/154 |
| 2009/0308907 A1 | 12/2009 | Nalagatla et al. |
| 2010/0012703 A1 | 1/2010 | Calabrese et al. |
| 2010/0069942 A1 | 3/2010 | Shelton, IV |
| 2010/0127041 A1 | 5/2010 | Morgan et al. |
| 2010/0133317 A1 | 6/2010 | Shelton, IV et al. |
| 2010/0147921 A1 | 6/2010 | Olson |
| 2010/0147922 A1 | 6/2010 | Olson |
| 2010/0155453 A1 | 6/2010 | Bombard et al. |
| 2010/0193566 A1 | 8/2010 | Scheib et al. |
| 2010/0224668 A1 | 9/2010 | Fontayne et al. |
| 2010/0249802 A1 | 9/2010 | May et al. |
| 2010/0252611 A1 | 10/2010 | Ezzat et al. |
| 2011/0006101 A1 | 1/2011 | Hall et al. |
| 2011/0024477 A1 | 2/2011 | Hall |
| 2011/0024478 A1 | 2/2011 | Shelton, IV |
| 2011/0036891 A1 | 2/2011 | Zemlok et al. |
| 2011/0087276 A1 | 4/2011 | Bedi et al. |
| 2011/0101069 A1 | 5/2011 | Bombard et al. |
| 2011/0114702 A1 | 5/2011 | Farascioni |
| 2011/0121049 A1 | 5/2011 | Malinouskas et al. |
| 2011/0147433 A1 | 6/2011 | Shelton, IV et al. |
| 2011/0155787 A1 | 6/2011 | Baxter, III et al. |
| 2011/0163146 A1 | 7/2011 | Ortiz et al. |
| 2011/0163149 A1 | 7/2011 | Viola |
| 2011/0192881 A1 | 8/2011 | Balbierz et al. |
| 2011/0192882 A1 | 8/2011 | Hess et al. |
| 2011/0192883 A1 | 8/2011 | Whitman et al. |
| 2011/0204119 A1 | 8/2011 | McCuen |
| 2011/0278343 A1 | 11/2011 | Knodel et al. |
| 2011/0290856 A1 | 12/2011 | Shelton, IV et al. |
| 2012/0016362 A1 | 1/2012 | Heinrich et al. |
| 2012/0053406 A1 | 3/2012 | Conlon et al. |
| 2012/0061446 A1 | 3/2012 | Knodel et al. |
| 2012/0074200 A1 | 3/2012 | Schmid et al. |
| 2012/0080478 A1 | 4/2012 | Morgan et al. |
| 2012/0080495 A1 | 4/2012 | Holcomb et al. |
| 2012/0080498 A1 | 4/2012 | Shelton, IV et al. |
| 2012/0091183 A1 | 4/2012 | Manoux et al. |
| 2012/0138659 A1 | 6/2012 | Marczyk et al. |
| 2012/0175399 A1 | 7/2012 | Shelton et al. |
| 2012/0181322 A1 | 7/2012 | Whitman et al. |

(56) References Cited

U.S. PATENT DOCUMENTS

| | | |
|---|---|---|
| 2012/0187179 A1 | 7/2012 | Gleiman |
| 2012/0193394 A1 | 8/2012 | Holcomb et al. |
| 2012/0193399 A1 | 8/2012 | Holcomb et al. |
| 2012/0199632 A1 | 8/2012 | Spivey et al. |
| 2012/0211542 A1 | 8/2012 | Racenet |
| 2012/0223121 A1 | 9/2012 | Viola et al. |
| 2012/0234895 A1 | 9/2012 | O'Connor et al. |
| 2012/0234897 A1 | 9/2012 | Shelton, IV et al. |
| 2012/0241492 A1 | 9/2012 | Shelton, IV et al. |
| 2012/0241493 A1 | 9/2012 | Baxter, III et al. |
| 2012/0241504 A1 | 9/2012 | Soltz et al. |
| 2012/0248169 A1 | 10/2012 | Widenhouse et al. |
| 2012/0286021 A1 | 11/2012 | Kostrzewski |
| 2012/0286022 A1 | 11/2012 | Olson et al. |
| 2012/0298722 A1 | 11/2012 | Hess et al. |
| 2013/0008937 A1 | 1/2013 | Viola |
| 2013/0012983 A1 | 1/2013 | Kleyman |
| 2013/0015231 A1 | 1/2013 | Kostrzewski |
| 2013/0020375 A1 | 1/2013 | Shelton, IV et al. |
| 2013/0020376 A1 | 1/2013 | Shelton, IV et al. |
| 2013/0026208 A1 | 1/2013 | Shelton, IV et al. |
| 2013/0026210 A1 | 1/2013 | Shelton, IV et al. |
| 2013/0032626 A1 | 2/2013 | Smith et al. |
| 2013/0037595 A1 | 2/2013 | Gupta et al. |
| 2013/0041406 A1 | 2/2013 | Bear et al. |
| 2013/0068815 A1 | 3/2013 | Bruewer et al. |
| 2013/0068816 A1 | 3/2013 | Mandakolathur Vasudevan et al. |
| 2013/0068818 A1 | 3/2013 | Kasvikis |
| 2013/0075447 A1 | 3/2013 | Weisenburgh, II et al. |
| 2013/0092717 A1 | 4/2013 | Marczyk et al. |
| 2013/0098964 A1 | 4/2013 | Smith et al. |
| 2013/0098966 A1 | 4/2013 | Kostrzewski et al. |
| 2013/0098970 A1 | 4/2013 | Racenet et al. |
| 2013/0105545 A1 | 5/2013 | Burbank |
| 2013/0105548 A1 | 5/2013 | Hodgkinson et al. |
| 2013/0105552 A1 | 5/2013 | Weir et al. |
| 2013/0105553 A1 | 5/2013 | (Tarinelli) Racenet et al. |
| 2013/0112730 A1 | 5/2013 | Whitman et al. |
| 2013/0119109 A1 | 5/2013 | Farascioni et al. |
| 2013/0146641 A1 | 6/2013 | Shelton, IV et al. |
| 2013/0146642 A1 | 6/2013 | Shelton, IV et al. |
| 2013/0153636 A1 | 6/2013 | Shelton, IV et al. |
| 2013/0153641 A1 | 6/2013 | Shelton, IV et al. |
| 2013/0161374 A1 | 6/2013 | Swayze et al. |
| 2013/0175316 A1 | 7/2013 | Thompson et al. |
| 2013/0193188 A1 | 8/2013 | Shelton, IV et al. |
| 2013/0256380 A1 | 10/2013 | Schmid et al. |
| 2013/0277410 A1 | 10/2013 | Fernandez et al. |
| 2013/0334280 A1 | 12/2013 | Krehel et al. |
| 2014/0014704 A1 | 1/2014 | Onukuri et al. |
| 2014/0014707 A1 | 1/2014 | Onukuri et al. |
| 2014/0021242 A1 | 1/2014 | Hodgkinson et al. |
| 2014/0048580 A1 | 2/2014 | Merchant et al. |
| 2014/0061280 A1 | 3/2014 | Ingmanson et al. |
| 2014/0076955 A1 | 3/2014 | Lorenz |
| 2014/0131419 A1 | 5/2014 | Bettuchi |
| 2014/0138423 A1 | 5/2014 | Whitfield et al. |
| 2014/0151431 A1 | 6/2014 | Hodgkinson et al. |
| 2014/0166720 A1 | 6/2014 | Chowaniec et al. |
| 2014/0166721 A1 | 6/2014 | Stevenson et al. |
| 2014/0166724 A1 | 6/2014 | Schellin et al. |
| 2014/0166725 A1 | 6/2014 | Schellin et al. |
| 2014/0166726 A1 | 6/2014 | Schellin et al. |
| 2014/0175146 A1 | 6/2014 | Knodel |
| 2014/0175150 A1 | 6/2014 | Shelton, IV et al. |
| 2014/0203062 A1 | 7/2014 | Viola |
| 2014/0239036 A1 | 8/2014 | Zerkle et al. |
| 2014/0239037 A1 | 8/2014 | Boudreaux et al. |
| 2014/0239038 A1 | 8/2014 | Leimbach et al. |
| 2014/0239040 A1 | 8/2014 | Fanelli et al. |
| 2014/0239041 A1 | 8/2014 | Zerkle et al. |
| 2014/0239043 A1 | 8/2014 | Simms et al. |
| 2014/0239044 A1 | 8/2014 | Hoffman |
| 2014/0239047 A1 | 8/2014 | Hodgkinson et al. |
| 2014/0246471 A1 | 9/2014 | Jaworek et al. |
| 2014/0246472 A1 | 9/2014 | Kimsey et al. |
| 2014/0246475 A1 | 9/2014 | Hall et al. |
| 2014/0246478 A1 | 9/2014 | Baber et al. |
| 2014/0252062 A1 | 9/2014 | Mozdzierz |
| 2014/0252064 A1 | 9/2014 | Mozdzierz et al. |
| 2014/0252065 A1 | 9/2014 | Hessler et al. |
| 2014/0263539 A1 | 9/2014 | Leimbach et al. |
| 2014/0263540 A1 | 9/2014 | Covach et al. |
| 2014/0263541 A1 | 9/2014 | Leimbach et al. |
| 2014/0263542 A1 | 9/2014 | Leimbach et al. |
| 2014/0263544 A1 | 9/2014 | Ranucci et al. |
| 2014/0263546 A1 | 9/2014 | Aranyi |
| 2014/0263550 A1 | 9/2014 | Aranyi et al. |
| 2014/0263552 A1 | 9/2014 | Hall et al. |
| 2014/0263553 A1 | 9/2014 | Leimbach et al. |
| 2014/0263554 A1 | 9/2014 | Leimbach et al. |
| 2014/0263555 A1 | 9/2014 | Hufnagel et al. |
| 2014/0263557 A1 | 9/2014 | Schaller |
| 2014/0263558 A1 | 9/2014 | Hausen et al. |
| 2014/0263562 A1 | 9/2014 | Patel et al. |
| 2014/0263564 A1 | 9/2014 | Leimbach et al. |
| 2014/0263565 A1 | 9/2014 | Lytle, IV et al. |
| 2014/0263566 A1 | 9/2014 | Williams et al. |
| 2014/0263570 A1 | 9/2014 | Hopkins et al. |
| 2014/0284371 A1 | 9/2014 | Morgan et al. |
| 2014/0291379 A1 | 10/2014 | Schellin et al. |
| 2014/0291380 A1 | 10/2014 | Meaner et al. |
| 2014/0291383 A1 | 10/2014 | Spivey et al. |
| 2014/0303668 A1 | 10/2014 | Nicholas et al. |
| 2014/0309665 A1 | 10/2014 | Parihar et al. |
| 2014/0332578 A1 | 11/2014 | Fernandez et al. |
| 2014/0336677 A1* | 11/2014 | Hessler ............... A61B 17/072 606/144 |
| 2014/0339286 A1 | 11/2014 | Motooka et al. |
| 2014/0353358 A1 | 12/2014 | Shelton, IV et al. |
| 2014/0367445 A1 | 12/2014 | Ingmanson et al. |
| 2014/0367446 A1 | 12/2014 | Ingmanson et al. |
| 2015/0048143 A1 | 2/2015 | Scheib et al. |
| 2015/0053740 A1 | 2/2015 | Shelton, IV |
| 2015/0053742 A1 | 2/2015 | Shelton, IV et al. |
| 2015/0053744 A1 | 2/2015 | Swayze et al. |
| 2015/0060517 A1 | 3/2015 | Williams |
| 2015/0076205 A1 | 3/2015 | Zergiebel |
| 2015/0076211 A1 | 3/2015 | Irka et al. |
| 2015/0080912 A1 | 3/2015 | Sapre |
| 2015/0133996 A1 | 5/2015 | Shelton, IV et al. |
| 2015/0134076 A1 | 5/2015 | Shelton, IV et al. |
| 2015/0150556 A1 | 6/2015 | McCuen |
| 2015/0157321 A1 | 6/2015 | Zergiebel et al. |
| 2015/0173744 A1 | 6/2015 | Shelton, IV et al. |
| 2015/0173745 A1 | 6/2015 | Baxter, III et al. |
| 2015/0173746 A1 | 6/2015 | Baxter, III et al. |
| 2015/0173747 A1 | 6/2015 | Baxter, III et al. |
| 2015/0173748 A1 | 6/2015 | Marczyk et al. |
| 2015/0173749 A1 | 6/2015 | Shelton, IV et al. |
| 2015/0173750 A1 | 6/2015 | Shelton, IV et al. |
| 2015/0173755 A1 | 6/2015 | Baxter, III et al. |
| 2015/0173756 A1 | 6/2015 | Baxter, III et al. |
| 2015/0173760 A1 | 6/2015 | Shelton, IV et al. |
| 2015/0173761 A1 | 6/2015 | Shelton, IV et al. |
| 2015/0182220 A1 | 7/2015 | Yates et al. |
| 2015/0209040 A1 | 7/2015 | Whitman et al. |
| 2015/0250474 A1 | 9/2015 | Abbott et al. |
| 2015/0297225 A1 | 10/2015 | Huitema et al. |
| 2015/0316431 A1 | 11/2015 | Collins et al. |
| 2015/0351765 A1 | 12/2015 | Valentine et al. |
| 2015/0359534 A1 | 12/2015 | Gibbons, Jr. |
| 2015/0366560 A1 | 12/2015 | Chen et al. |
| 2015/0374371 A1 | 12/2015 | Richard et al. |
| 2015/0374372 A1 | 12/2015 | Zergiebel et al. |
| 2015/0374376 A1 | 12/2015 | Shelton, IV |
| 2016/0030040 A1 | 2/2016 | Calderoni et al. |
| 2016/0051259 A1 | 2/2016 | Hopkins et al. |
| 2016/0058443 A1 | 3/2016 | Yates et al. |
| 2016/0066907 A1 | 3/2016 | Cheney et al. |
| 2016/0067074 A1 | 3/2016 | Thompson et al. |
| 2016/0089137 A1 | 3/2016 | Hess et al. |
| 2016/0095585 A1 | 4/2016 | Zergiebel et al. |
| 2016/0100835 A1 | 4/2016 | Linder et al. |

(56) References Cited

U.S. PATENT DOCUMENTS

| | | | |
|---|---|---|---|
| 2016/0106406 A1 | 4/2016 | Cabrera et al. |
| 2016/0113647 A1 | 4/2016 | Hodgkinson |
| 2016/0113648 A1 | 4/2016 | Zergiebel et al. |
| 2016/0113649 A1 | 4/2016 | Zergiebel et al. |
| 2016/0120542 A1 | 5/2016 | Westling et al. |
| 2016/0166249 A1 | 6/2016 | Knodel |
| 2016/0166253 A1 | 6/2016 | Knodel |
| 2016/0199064 A1 | 7/2016 | Shelton, IV et al. |
| 2016/0199084 A1 | 7/2016 | Takei |
| 2016/0206315 A1 | 7/2016 | Olson |
| 2016/0206336 A1 | 7/2016 | Frushour |
| 2016/0235494 A1 | 8/2016 | Shelton, IV et al. |
| 2016/0242773 A1 | 8/2016 | Sadowski et al. |
| 2016/0242774 A1 | 8/2016 | Ebner |
| 2016/0242779 A1 | 8/2016 | Aranyi et al. |
| 2016/0249915 A1 | 9/2016 | Beckman et al. |
| 2016/0249916 A1 | 9/2016 | Shelton, IV et al. |
| 2016/0249918 A1 | 9/2016 | Shelton, IV et al. |
| 2016/0249927 A1 | 9/2016 | Beckman et al. |
| 2016/0249929 A1 | 9/2016 | Cappola et al. |
| 2016/0249945 A1 | 9/2016 | Shelton, IV et al. |
| 2016/0256071 A1 | 9/2016 | Shelton, IV et al. |
| 2016/0256152 A1 | 9/2016 | Kostrzewski |
| 2016/0256154 A1 | 9/2016 | Shelton, IV et al. |
| 2016/0256160 A1 | 9/2016 | Shelton, IV et al. |
| 2016/0256161 A1 | 9/2016 | Overmyer et al. |
| 2016/0256162 A1 | 9/2016 | Shelton, IV et al. |
| 2016/0256163 A1 | 9/2016 | Shelton, IV et al. |
| 2016/0256184 A1 | 9/2016 | Shelton, IV et al. |
| 2016/0256185 A1 | 9/2016 | Shelton, IV et al. |
| 2016/0256187 A1 | 9/2016 | Shelton, IV et al. |
| 2016/0262750 A1 | 9/2016 | Hausen et al. |
| 2016/0270783 A1 | 9/2016 | Yigit et al. |
| 2016/0270788 A1 | 9/2016 | Czernik |
| 2016/0278764 A1 | 9/2016 | Shelton, IV et al. |
| 2016/0278765 A1 | 9/2016 | Shelton, IV et al. |
| 2016/0278771 A1 | 9/2016 | Shelton, IV et al. |
| 2016/0278774 A1 | 9/2016 | Shelton, IV et al. |
| 2016/0278775 A1 | 9/2016 | Shelton, IV et al. |
| 2016/0278777 A1 | 9/2016 | Shelton, IV et al. |
| 2016/0278848 A1 | 9/2016 | Boudreaux et al. |
| 2016/0287250 A1 | 10/2016 | Shelton, IV et al. |
| 2016/0287251 A1 | 10/2016 | Shelton, IV et al. |
| 2016/0296216 A1 | 10/2016 | Nicholas et al. |
| 2016/0296226 A1 | 10/2016 | Kostrzewski |
| 2016/0302791 A1 | 10/2016 | Schmitt |
| 2016/0310134 A1 | 10/2016 | Contini et al. |
| 2016/0324514 A1 | 11/2016 | Srinivas et al. |
| 2016/0324518 A1 | 11/2016 | Nicholas et al. |
| 2016/0338703 A1 | 11/2016 | Scirica et al. |
| 2016/0345971 A1 | 12/2016 | Bucciaglia et al. |
| 2016/0345973 A1 | 12/2016 | Marczyk et al. |
| 2016/0354176 A1 | 12/2016 | Schmitt |
| 2016/0374678 A1 | 12/2016 | Becerra et al. |
| 2017/0000483 A1 | 1/2017 | Motai et al. |
| 2017/0020525 A1 | 1/2017 | Shah |
| 2017/0095257 A1 | 4/2017 | Miller et al. |

FOREIGN PATENT DOCUMENTS

| | | |
|---|---|---|
| CA | 2884962 A1 | 11/2015 |
| DE | 2744824 A1 | 4/1978 |
| DE | 2903159 A1 | 7/1980 |
| DE | 3114135 A1 | 10/1982 |
| DE | 1213426 A1 | 10/1992 |
| DE | 1300307 A1 | 7/1994 |
| EP | 0041022 A1 | 12/1981 |
| EP | 0136950 A2 | 4/1985 |
| EP | 0140552 A2 | 5/1985 |
| EP | 0156774 A2 | 10/1985 |
| EP | 0213817 A1 | 3/1987 |
| EP | 0216532 A1 | 4/1987 |
| EP | 0220029 A1 | 4/1987 |
| EP | 0273468 A2 | 7/1988 |
| EP | 0324166 A2 | 7/1989 |
| EP | 0324635 A1 | 7/1989 |
| EP | 0324637 A1 | 7/1989 |
| EP | 0324638 A1 | 7/1989 |
| EP | 0365153 A1 | 4/1990 |
| EP | 0369324 A1 | 5/1990 |
| EP | 0373762 A1 | 6/1990 |
| EP | 0380025 A2 | 8/1990 |
| EP | 0399701 A1 | 11/1990 |
| EP | 0449394 A2 | 10/1991 |
| EP | 0484677 A1 | 5/1992 |
| EP | 0489436 A1 | 6/1992 |
| EP | 0503662 A1 | 9/1992 |
| EP | 0514139 A2 | 11/1992 |
| EP | 0536903 A2 | 4/1993 |
| EP | 0537572 A2 | 4/1993 |
| EP | 0539762 A1 | 5/1993 |
| EP | 0.545029 A1 | 6/1993 |
| EP | 0552050 A2 | 7/1993 |
| EP | 0552423 A2 | 7/1993 |
| EP | 0579038 A1 | 1/1994 |
| EP | 0589306 A2 | 3/1994 |
| EP | 0591946 A1 | 4/1994 |
| EP | 0592243 A2 | 4/1994 |
| EP | 0593920 A1 | 4/1994 |
| EP | 0598202 A1 | 5/1994 |
| EP | 0598579 A1 | 5/1994 |
| EP | 0600182 A2 | 6/1994 |
| EP | 0621006 A1 | 10/1994 |
| EP | 0621009 A1 | 10/1994 |
| EP | 0656188 A2 | 6/1995 |
| EP | 0666057 A2 | 8/1995 |
| EP | 0705571 A1 | 4/1996 |
| EP | 0760230 A1 | 3/1997 |
| EP | 1952769 A2 | 8/2008 |
| EP | 2090253 A2 | 8/2009 |
| EP | 2090254 A1 | 8/2009 |
| EP | 2583630 A2 | 4/2013 |
| EP | 2586382 A2 | 5/2013 |
| EP | 2907456 A1 | 8/2015 |
| FR | 391239 A | 10/1908 |
| FR | 2542188 A | 9/1984 |
| FR | 2660851 A1 | 10/1991 |
| FR | 2681775 A1 | 4/1993 |
| GB | 1352554 A | 5/1974 |
| GB | 1452185 A | 10/1976 |
| GB | 1555455 A | 11/1979 |
| GB | 2048685 A | 12/1980 |
| GB | 2070499 A | 9/1981 |
| GB | 2141066 A | 12/1984 |
| GB | 2165559 A | 4/1986 |
| JP | 51149985 | 12/1976 |
| JP | 2001087272 | 4/2001 |
| SU | 559146 A1 | 4/1979 |
| SU | 728848 A1 | 4/1980 |
| SU | 380703 A1 | 12/1982 |
| SU | 390220 A1 | 1/1983 |
| WO | 2008302247 | 7/1983 |
| WO | 3910094 A1 | 11/1989 |
| WO | 3210976 A1 | 7/1992 |
| WO | 9308754 A1 | 5/1993 |
| WO | 9314706 A1 | 8/1993 |
| WO | 2004/032760 A2 | 4/2004 |
| WO | 2009071070 A2 | 6/2009 |
| WO | 20150191887 A1 | 12/2015 |

\* cited by examiner

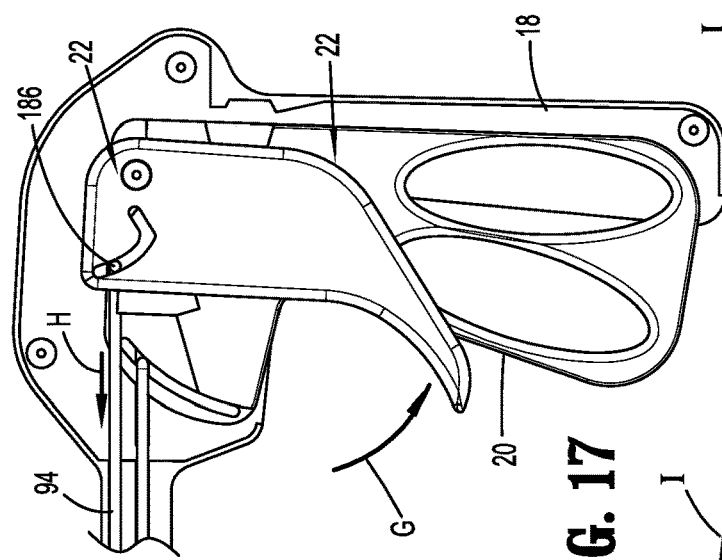
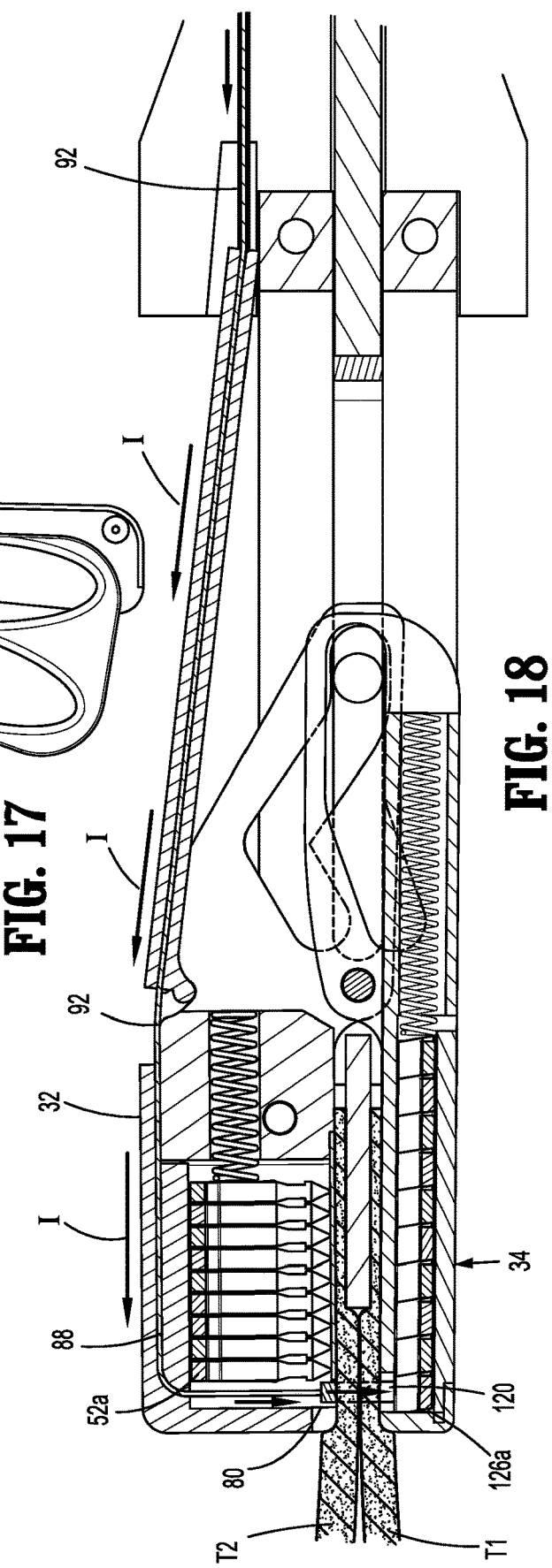
FIG. 17
FIG. 18

SURGICAL STAPLING DEVICE WITH INDEPENDENTLY MOVABLE JAWS

CROSS-REFERENCE TO RELATED APPLICATIONS

This application claims the benefit of and priority to U.S. Provisional Patent Application Ser. No. 62/811,925 filed Feb. 28, 2019, the entire disclosure of which is incorporated by reference herein

BACKGROUND

1. Technical Description

The present disclosure is directed to stapling devices and, more particularly, to stapling devices that includes two independently movable jaws for connecting two tissue segments together.

2. Background of Related Art

Surgical stapling devices for joining tissue segments are known in the art and typically include first and second jaws that are movable in relation to each other to clamp and staple tissue. In certain surgical procedures, e.g., vaginal cuff closure procedures, it is necessary to move the two tissue segments in closer proximity to each other before the tissue segments can be clamped and stapled. In known staplers that have two jaws that are moved to a clamped position, it is necessary to use graspers or the like to reposition the tissue segments prior to clamping and stapling the tissue segments. Where the surgical procedure is being performed laparoscopically, additional access ports are required to provide access to the surgical site for the graspers.

A continuing need exists in the art for a surgical stapling device that can independently grip and reposition two tissue segments prior to joining the tissue segments.

SUMMARY

One aspect of the present disclosure is directed to a surgical stapling device including an elongate body and a tool assembly. The elongate body has a distal portion and a proximal portion. The tool assembly is supported on the distal portion of the elongate body and includes a stationary jaw, a top jaw positioned on one side of the stationary jaw, and a bottom jaw positioned on an opposite side of the stationary jaw. The top jaw is movable in relation to the stationary jaw independently of the bottom jaw between an open position and a clamped position to clamp tissue between the top jaw and the stationary jaw, and the bottom jaw is movable in relation to the stationary jaw independently of the top jaw between an open position and a clamped position to clamp tissue between the bottom jaw and the stationary jaw.

In embodiments, the top jaw supports a plurality of staples.

In some embodiments, a staple pusher extends within the top jaw and is movable to eject a distal-most staple of the plurality of staples from the top jaw towards the bottom jaw.

In certain embodiments, the bottom jaw supports a plurality of staple retainers, wherein each of the plurality of staple retainers is engageable with a respective one of the plurality of staples to secure each of the plurality of staples to tissue.

In embodiments, the surgical stapling device includes an actuator that is operably associated with the top jaw and is movable from an advanced position towards a retracted position to move the top jaw from the open position to the clamped position.

In some embodiments, the actuator is operably associated with the bottom jaw and is movable to move the bottom jaw from the open position to the clamped position.

In certain embodiments, the surgical stapling device includes a clamp rod having a distal portion connected to the actuator, wherein the clamp rod is movable from an advanced position to a retracted position to move the actuator from the advanced position to the retracted position.

In embodiments, the top jaw includes a first camming slot, the bottom jaw includes a second camming slot, and the actuator includes a cam member, wherein the cam member is movable within the first and second camming slots to move the top and bottom jaws from the open positions to the clamped positions.

In some embodiments, the first and second camming slots are configured such that movement of the actuator from the advanced position to an intermediate position moves the top jaw from the open position to the clamped position and movement of the actuator from the intermediate position to the retracted position moves the bottom jaw from the open position to the clamped position.

In certain embodiments, the surgical stapling device includes a handle assembly having a clamping trigger that is connected to the actuator by a clamp rod, wherein the clamping trigger can be pivoted from a non-actuated position to a partially actuated position to move the top jaw from the open position to the clamped position and can be pivoted from the partially actuated position to a fully actuated position to move the bottom jaw from the open position to the clamped position.

In embodiments, a staple pusher extends within the top jaw and is movable from a retracted position to an advanced position to eject one of the plurality of staples from the top jaw towards the bottom jaw.

In some embodiments, the handle assembly includes a firing trigger that is connected to the staple pusher by a firing rod, wherein the firing trigger is movable from a non-actuated position to an actuated position to move the staple pusher from the retracted position to the advanced position.

In certain embodiments, the clamping trigger includes a lock member that is positioned to prevent advancement of the firing rod until the clamping trigger is moved to the fully actuated position.

Another aspect of the present disclosure is directed to a method of performing a surgical procedure including positioning a tool assembly of a surgical device adjacent a first tissue segment such that the first tissue segment is positioned between a top jaw of the tool assembly and a stationary jaw of the tool assembly; moving an actuator of the surgical device to move the top jaw towards the stationary jaw to clamp the first tissue segment between the top jaw and the stationary jaw; moving the tool assembly towards a second tissue segment to move the first tissue segment towards the second tissue segment; positioning the tool assembly of the surgical device adjacent the second tissue segment such that the second tissue segment is positioned between a bottom jaw of the tool assembly and the stationary jaw of the tool assembly; moving the actuator of the surgical device to move the bottom jaw towards the stationary jaw to clamp the second tissue segment between the bottom jaw and the stationary jaw; and moving a firing rod to eject a staple from the first jaw through the first and second tissue segments towards the second jaw to join the first tissue segment to the second tissue segment.

In embodiments, moving the actuator of the surgical device to move the top jaw towards the stationary jaw includes moving the actuator from an advanced position to an intermediate position.

In some embodiments, moving the actuator of the surgical device to move the bottom jaw towards the stationary jaw includes moving the actuator from the intermediate position to a retracted position.

In certain embodiments, moving the actuator of the surgical device from the advanced position to the intermediate position includes grasping a first grip loop of a clamp trigger of a handle assembly and pulling the first grip loop towards a stationary handle of the handle assembly.

In embodiments, moving the actuator of the surgical device from the intermediate position to the retracted position includes grasping a second grip loop of the clamp trigger of the handle assembly and pulling the second grip loop towards the stationary handle of the handle assembly.

In some embodiments, moving the firing rod to eject the staple from the first jaw through the first and second tissue segments towards the second jaw to join the first tissue segment and the second tissue segment includes moving a firing trigger of a handle assembly towards a stationary handle of the handle assembly to advance the firing rod to advance a staple pusher supported within the top jaw.

BRIEF DESCRIPTION OF THE DRAWINGS

Various embodiments of the presently disclosed stapling device are described herein below with reference to the drawings, wherein:

FIG. 3A is an enlarged view of the indicated area of detail shown in FIG. 3;

FIG. 17 is a side view of the handle assembly of the stapling device shown in FIG. 13 with the clamp trigger in the fully actuated position and the firing trigger in the actuated position; and FIG. 18 is an enlarged view of the stapling device shown in FIG. 13 with the top and bottom jaws clamped and a staple pusher in an advanced position.

DETAILED DESCRIPTION OF EMBODIMENTS

Figure 1:
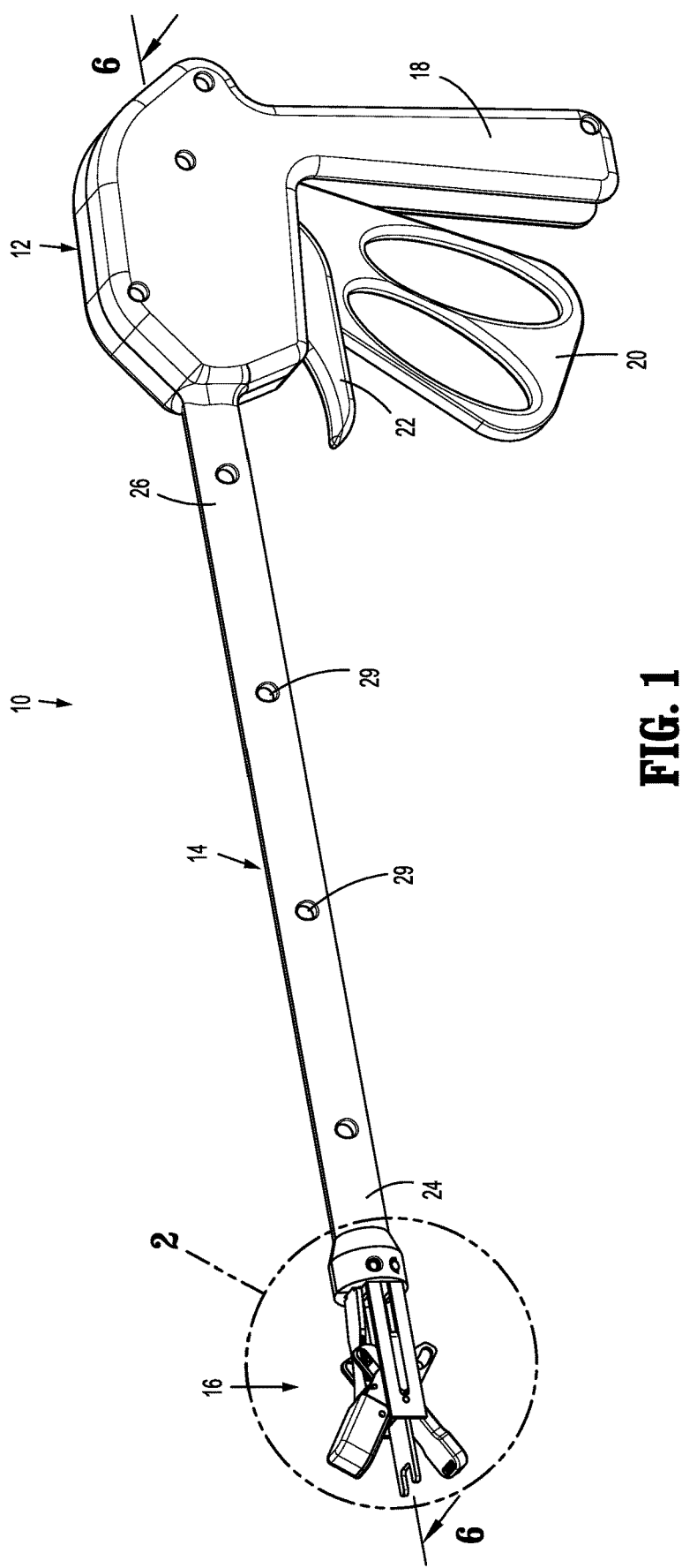
FIG. 1 is an exemplary embodiment of the presently disclosed surgical stapling device with top and bottom jaws in an open position.

The presently disclosed stapling device will now be described in detail with reference to the drawings in which like reference numerals designate identical or corresponding elements in each of the several views. However, it is to be understood that the disclosed embodiments are merely exemplary of the disclosure and may be embodied in various forms. Well-known functions or constructions are not described in detail to avoid obscuring the present disclosure in unnecessary detail. Therefore, specific structural and functional details disclosed herein are not to be interpreted as limiting, but merely as a basis for the claims and as a representative basis for teaching one skilled in the art to variously employ the present disclosure in virtually any appropriately detailed structure.

In this description, the term "proximal" is used generally to refer to that portion of the device that is closer to a clinician, while the term "distal" is used generally to refer to that portion of the device that is farther from the clinician. In addition, the term "endoscopic" is used generally used to refer to endoscopic, laparoscopic, arthroscopic, and/or any other procedure conducted through small diameter incision or cannula. Further, the term "clinician" is used generally to refer to medical personnel including doctors, nurses, and support personnel. It is also understood that all spatial references, such as, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior".

Referring to FIG. 1, the presently disclosed stapling device with independently movable jaws is shown generally as stapling device 10 and includes a handle assembly 12, an elongate body 14, and a tool assembly 16. The handle assembly 12 includes a stationary handle 18, a clamping trigger 20, and a firing trigger 22. The elongate body 14 extends distally from the handle assembly 12 and includes a distal portion 24 defining a mounting member 25 (FIG. 2) and a proximal portion 26. The proximal portion 26 is secured to the handle assembly 12 and the distal portion 24 supports the tool assembly 16. Although the handle assembly 12 is shown as a manually actuated device, it is envisioned that the stapling device 10 may be electrically actuated such as with an electric motor or coupled to a robotic system. In embodiments, the stationary handle 18 and the elongate body 14 are formed from integral half-sections 28a and 28b (FIG. 3). The half-sections 28a and 28b can be secured together using screws 29. Alternately, other securement techniques can be used to secure the half-sections 28a and 28b together.

Figure 2:
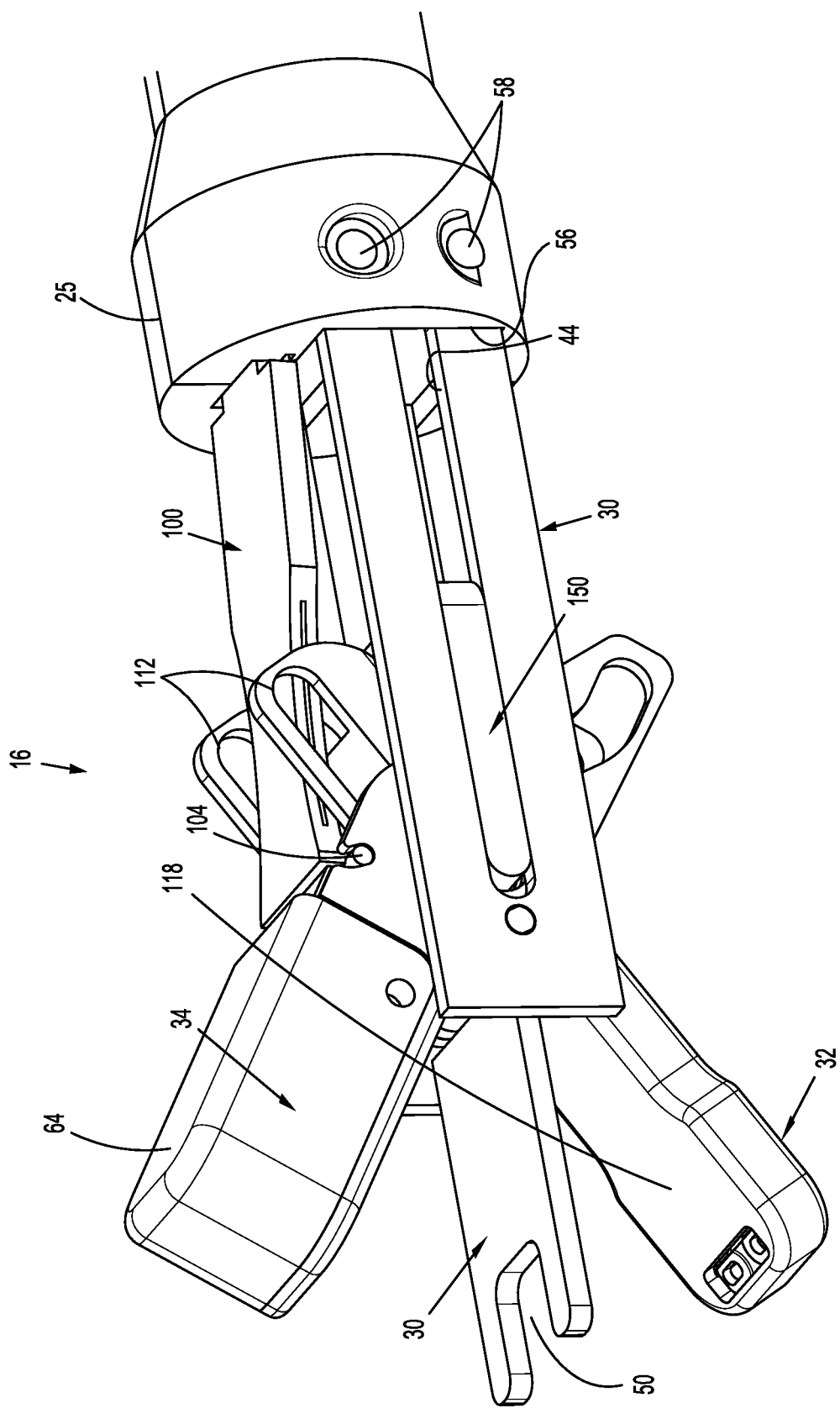
FIG. 2 is an enlarged view of the indicated area of detail shown in FIG. 1.
Figure 3:
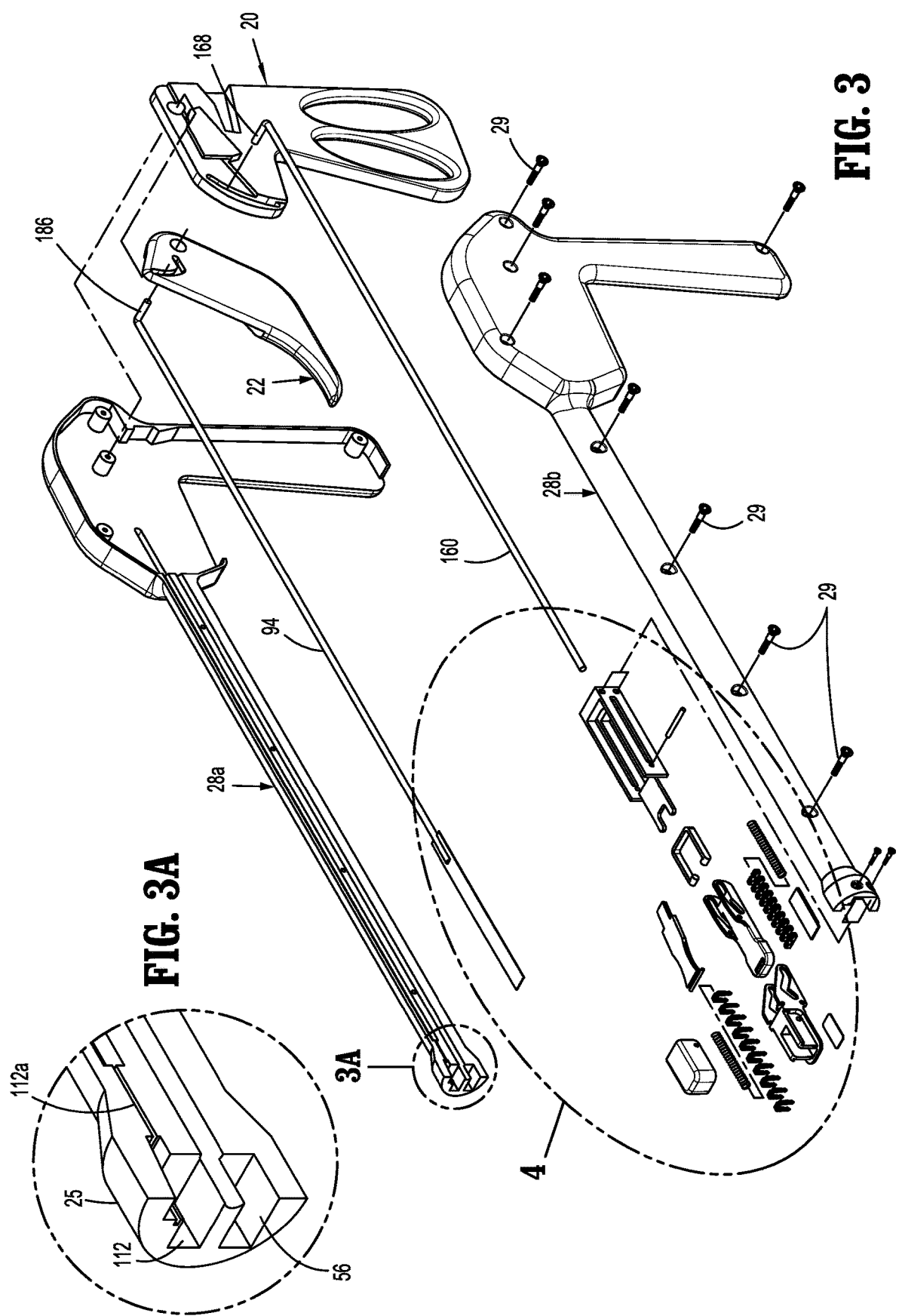
FIG. 3 is an exploded perspective view of the stapling device shown in FIG. 1.
Figure 4:
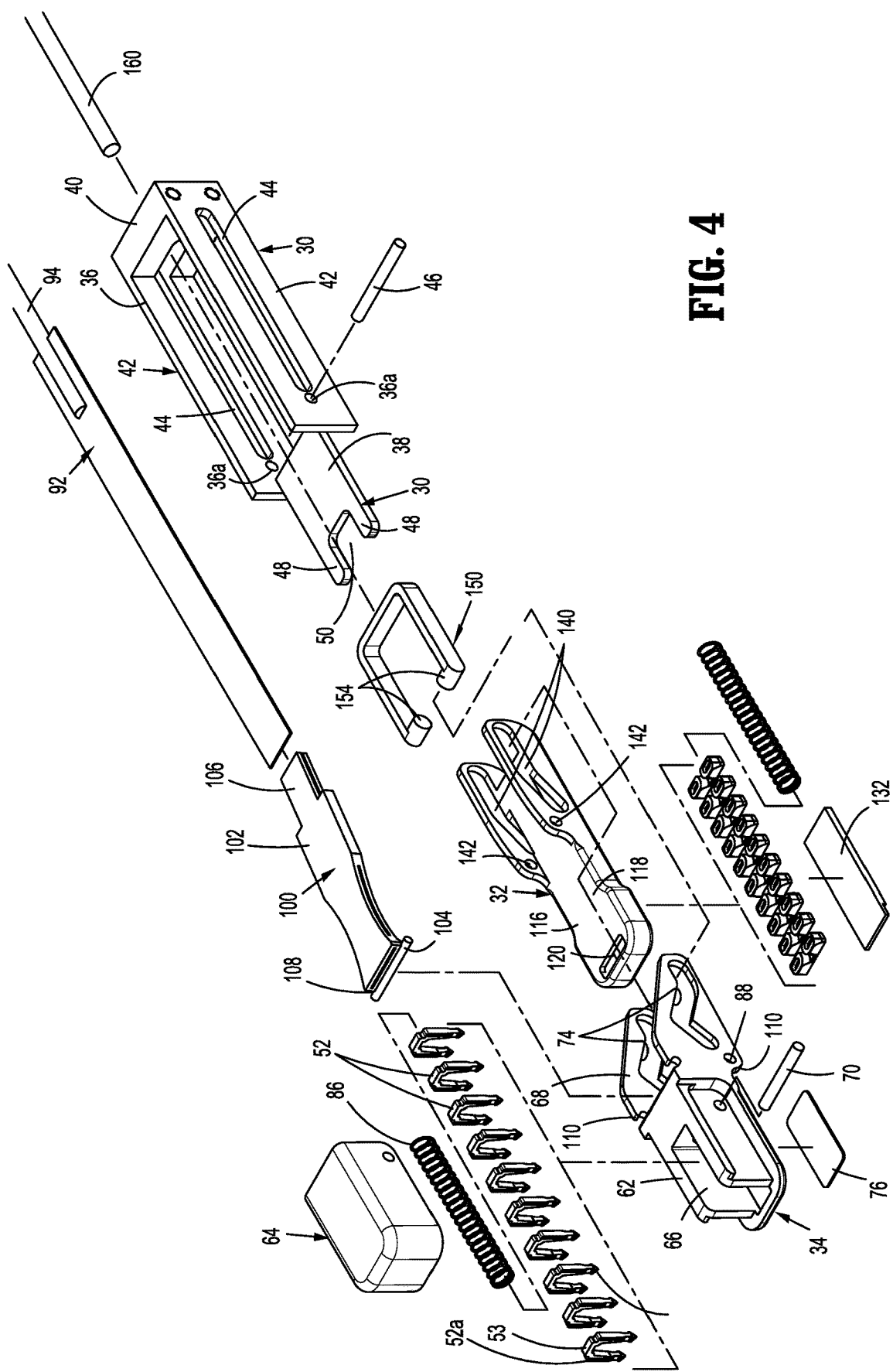
FIG. 4 is an enlarged view of the indicated area of detail shown in FIG. 3
Figure 5:
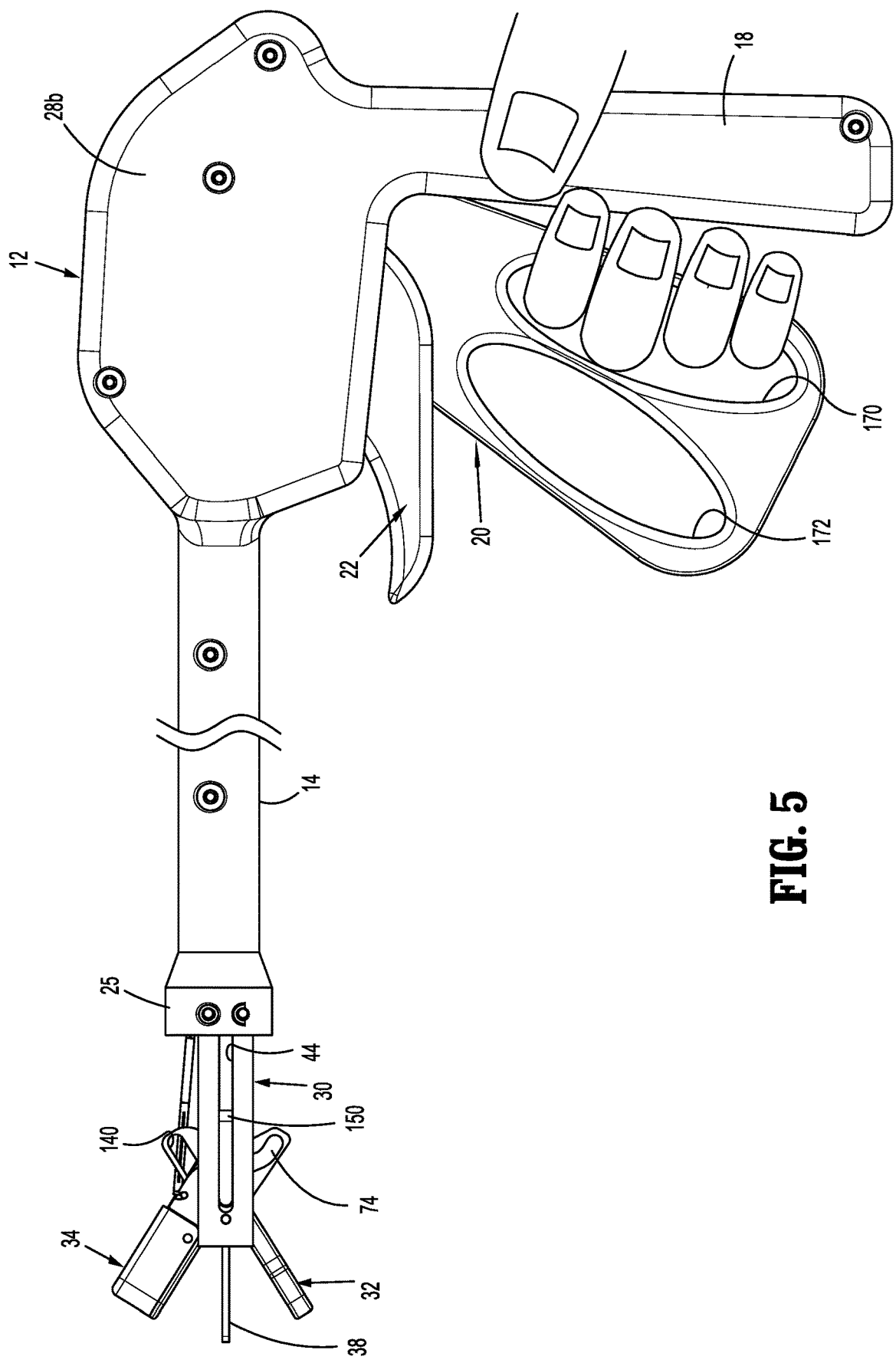
FIG. 5 is a side view of the stapling device shown in FIG. 1 with the top and bottom jaws of the stapling device in open positions.
Figure 6:
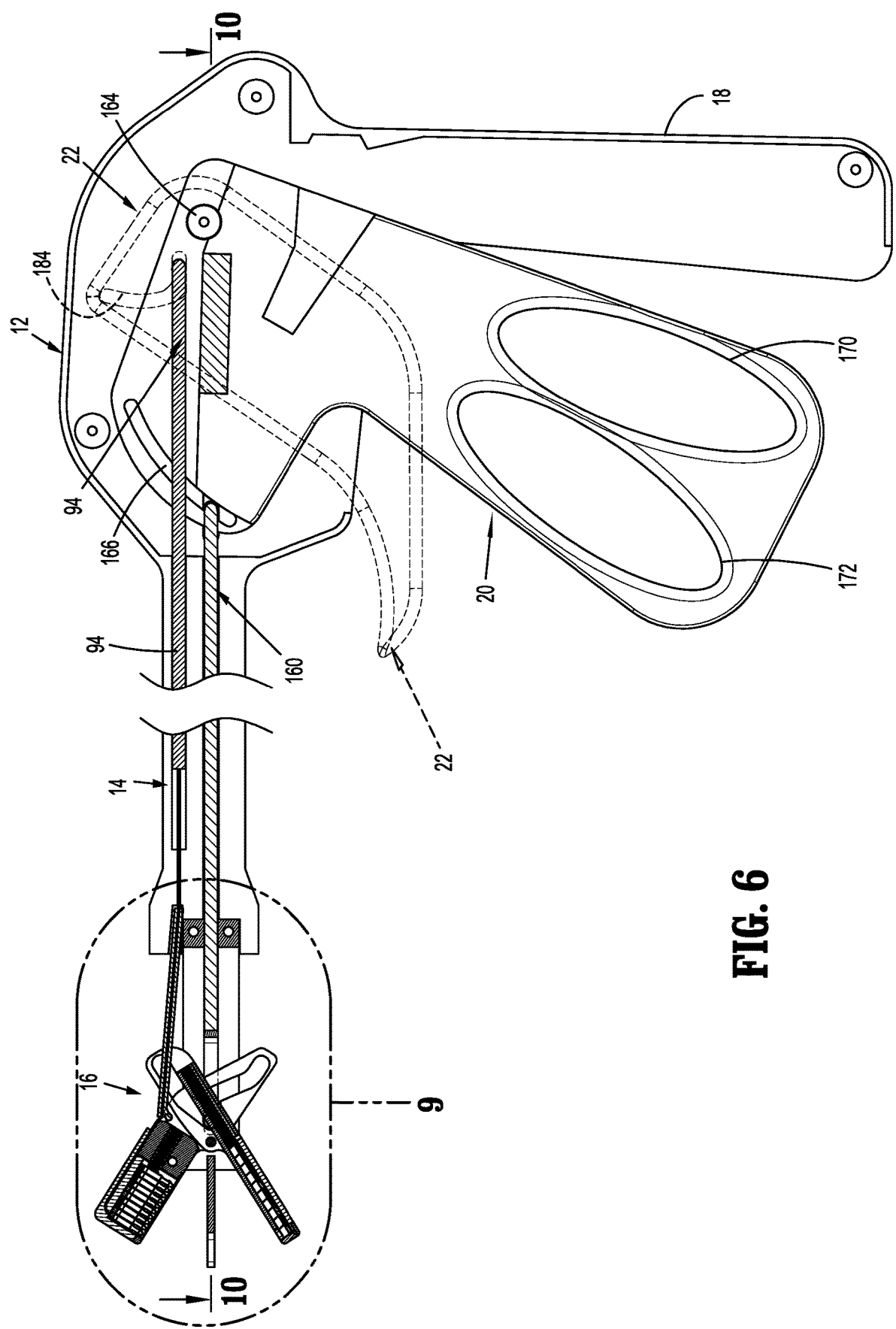
FIG. 6 is a cross-sectional view taken along section line 6-6 of FIG. 1.

Referring to FIGS. 2-4, the tool assembly 16 includes stationary jaw 30, a bottom jaw 32, and a top jaw 34. The stationary jaw 30 includes a housing 36 and a tissue plate 38 that extends distally from and is fixedly secured to the housing 36. The housing 36 has a box-like configuration defined by a rear wall 40 and spaced side walls 42. Each of the spaced side walls defines a linear slot 44 that extends along the length of the housing 36. The housing 36 includes a distal portion that defines openings 36a that receive a pivot member 46 that is provided to couple the top and bottom jaws 32 and 34 to the stationary jaw 30 as described in further detail below. In embodiments, the tissue plate 38 includes distal fingers 48 that are spaced from each other to define a slot 50 that is dimensioned to facilitate passage of staples 52.

The rear wall 40 of the housing 36 of the stationary jaw 30 is fixedly received within a first cutout 56 formed in mounting member 25 of the elongate body 14. In embodiments, the rear wall 40 of the stationary jaw 30 is fixedly secured within the first cutout 56 of the mounting member 25 using screws 58. Alternately, other fastening techniques can be used to secure the stationary jaw 30 to the mounting member 25 on the distal portion 24 of the elongate body 14.

The top jaw 34 includes a body 62 and a cover 64. The body 62 defines a staple receptacle 66 and spaced flanges 68 that extend proximally from the body 62. The staple receptacle 66 is dimensioned to receive a plurality of staples 52. The cover 64 is pivotally supported on the body 62 using a pivot member 70 such that the cover 64 can be pivoted to open or close the receptacle 66. The spaced flanges 68 each define a curved or non-linear cam slot 74 that will be described in further detail below. The body 62 defines a bore 72 that receives the pivot member 46 to pivotably secure the top jaw 34 to the stationary jaw 30.

In embodiments, the lower portion of the receptacle 66 is covered by a plate 76 (FIG. 4) that is secured to the body 62 of the top jaw 34. The plate 76 is spaced from a distal end of the top jaw 34 to define a slot 80. The slot 80 communicates with the receptacle 66 and is aligned with a distal-most staple 52a (FIG. 4) of the plurality of staples 52 and with the slot 50 in the tissue plate 38 of the stationary jaw 30 to allow a staple 52 to be ejected from the receptacle 66 and through the slot 50 towards the bottom jaw 32.

Figure 9:
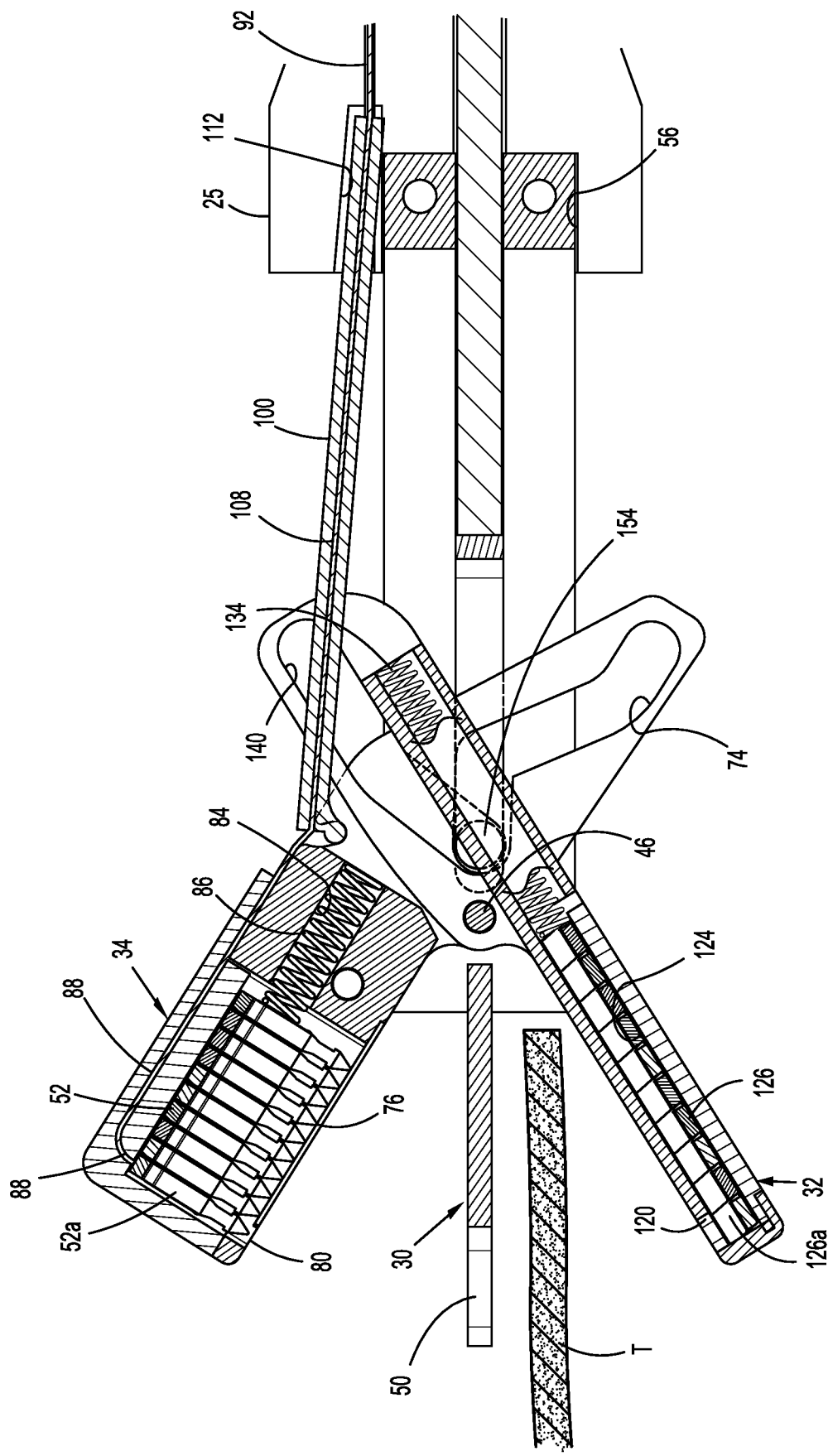
FIG. 9 is an enlarged view of the indicated area of detail shown in FIG. 6.

In some embodiments, the body 62 of the top jaw 34 defines a through bore 84 that receives a biasing member 86 that is positioned to urge the plurality of staples 52 towards a distal portion of the receptacle 66 such that the distal-most staple 52a (FIG. 4) is aligned with the slot 80 in the top jaw 34. The body 62 also defines a channel 88 that extends from a proximal portion of the body distally and communicates with the receptacle 66 at a position above the distal-most staple 52a (FIG. 9). The channel 88 is curved downwardly towards the stationary jaw 30 at a position above the slot 80.

Figure 14:
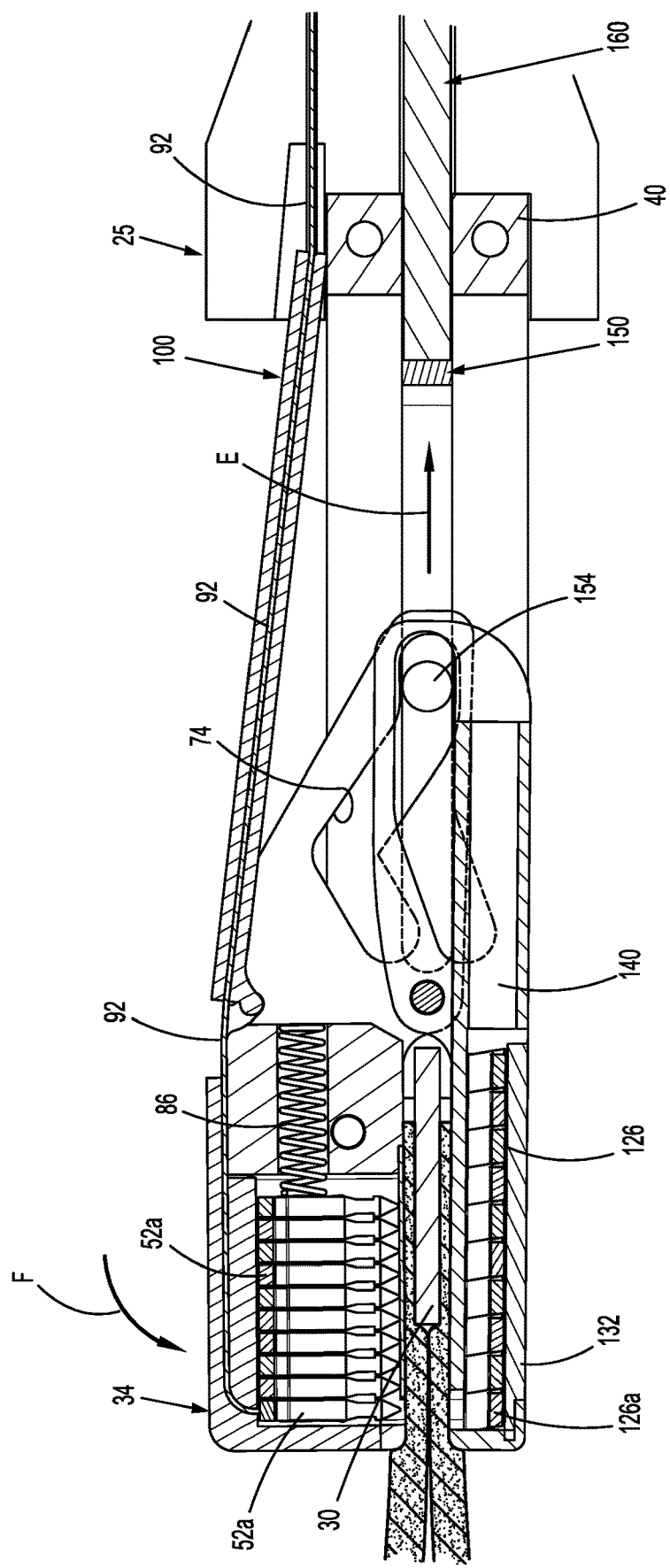
FIG. 14 is an enlarged view of the indicated area of detail shown in FIG. 13.

The tool assembly 16 includes a staple pusher 92 that includes a distal portion that is positioned within the channel 88 of the top jaw 34 and a proximal portion that is coupled to a firing rod 94. The staple pusher 92 is substantially flat and is formed of a flexible material to facilitate movement of the staple pusher 92 through the channel 88 of the top jaw 34. The staple pusher 92 is movable from a retracted position (FIG. 14) to an advanced position to eject the distal-most staple 52a (FIG. 4) from the top jaw 34. When the staple pusher 92 is in a retracted position, a distal end of the staple pusher 92 is positioned adjacent a back span 53 of the distal-most staple 52a (FIG. 14). When the staple pusher 92 is in the advanced position, the distal end of the staple pusher 92 is positioned adjacent the slot 80 in the top jaw 34 to eject the distal-most staple 52a from the receptacle 66 of the top jaw 34 through the slot 80 (FIG. 14).

The tool assembly 16 also includes a hinge guide 100 that includes a body 102 having a distal portion including a pivot pin 104 and a proximal portion including a proximal extension 106. The body 102 defines a through channel 108 (FIG. 4) that receives the staple pusher 92. The pivot pin 104 is received within U-shaped recesses 110 formed in the spaced flanges 68 of the top jaw 34, and the proximal extension 106 is positioned within a second cutout 112 (FIG. 3A) formed in the mounting member 25 of the elongate body 14. The second cutout 112 communicates with a channel 112a formed in the mounting member 25 that receives a proximal portion of the staple pusher. The second cutout 112 is dimensioned to facilitate pivotal movement of the hinge guide 100. More specifically, when the top jaw 34 is moved between the clamped position (FIG. 14) and the open position (FIG. 9), the second cutout 112 is dimensioned to allow the proximal extension 106 of the hinge guide 100 to pivot with the top jaw 34 as the top jaw 34 moves between the open and clamped positions.

The bottom jaw 32 includes a body 116 having a tissue plate 118 defining a distal slot 120 that is aligned with the slot 80 in the top jaw 34. In embodiments, the body 116 defines a cavity 124 (FIG. 9) that receives a plurality of staple retainers 126. The staple retainers 126 are configured to engage legs of the staples 52 to secure the staples 52 to tissue "T" (FIG. 9). The distal-most staple retainer 126a is aligned with the slot 120 in the bottom jaw 32 such that when the top and bottom jaws 34 and 32 are in the clamped position and the stapling device 10 is fired, as described in detail below, the distal-most staple 52a engages the distal-most staple retainer 126a to secure the staple 52a and the staple retainer 126a to tissue. It is also envisioned that the top jaw 34 can support traditional staples and that the bottom jaw can define an anvil plate that is positioned and configured to receive and deform the staples into a pre-determined configuration, e.g., B-shape.

The body 116 of the bottom jaw 32 has a bottom that defines an opening 130 that is positioned opposite to the tissue plate 118 and provides access to the cavity 124 defined by the bottom jaw 32. The opening 130 is covered by a plate 132 to retain the staple retainers 126 within the cavity 124. A biasing member 134 is proximally positioned within the cavity 124 to urge the staple retainers 126 towards the distal end of the cavity 124 to position the distal-most staple retainer in alignment with the slot 120 in the tissue plate 118 of the bottom jaw 32.

The bottom jaw 32 includes a proximal portion having spaced upstanding flanges 138. Each of the upstanding flanges 138 defines a curved or non-linear cam slot 140 that is described in detail below. Each of the flanges 138 of the bottom jaw 32 defines a bore 142 that receives the pivot member 46 to secure the bottom jaw 32 to the stationary jaw 30 and to the top jaw 34 such that the top and bottom jaws 34 and 32 can be independently pivoted in relation to the stationary jaw 30 between the open and clamped positions.

The stapling device 10 includes an actuator 150 that is movable between an advanced position and a retracted position within the tool assembly 16 to move the top and bottom jaws 34 and 32 between the open and clamped positions. In embodiments, the actuator includes a cam member 152 that is supported between the linear slots 44 of the housing 36 of the stationary jaw 30 for movement between the advanced and retracted positions. The cam member 152 includes fingers 154 that extend into the cam slots 74 of the top jaw 34 and the cam slots 140 of the bottom jaw 32. The linear slots 44 in the stationary jaw 30 limit movement of the actuator 150 to linear movement. Thus, as the fingers 154 move through the cam slots 74 and 140, the top and bottom jaws 34 and 32 are pivoted between the open and clamped positions. The cam slots 74 and 140 are configured such that movement of the actuator 150 within the linear slots 44 of the stationary jaw 30 from an advanced position to an intermediate position moves the bottom jaw 32 from the open position to the clamped position while the top jaw 34 remains stationary in relation to the stationary jaw 30, and movement of the actuator 150 from the intermediate position to the retracted position moves the top jaw 34 from the open position to the clamped position while the bottom jaw 32 remains in the clamped position.

The actuator 150 is coupled to a clamp rod 160 that extends from the handle assembly 12 to the tool assembly 16 through the elongate body 14. In embodiments, the clamp rod 160 has a distal portion that is secured to a proximal end of the actuator 150. The clamp rod 160 is coupled to the handle assembly 12 as described in further detail below and is movable between advanced and retracted positions to move the actuator between its advanced and retracted positions.

Figure 12:
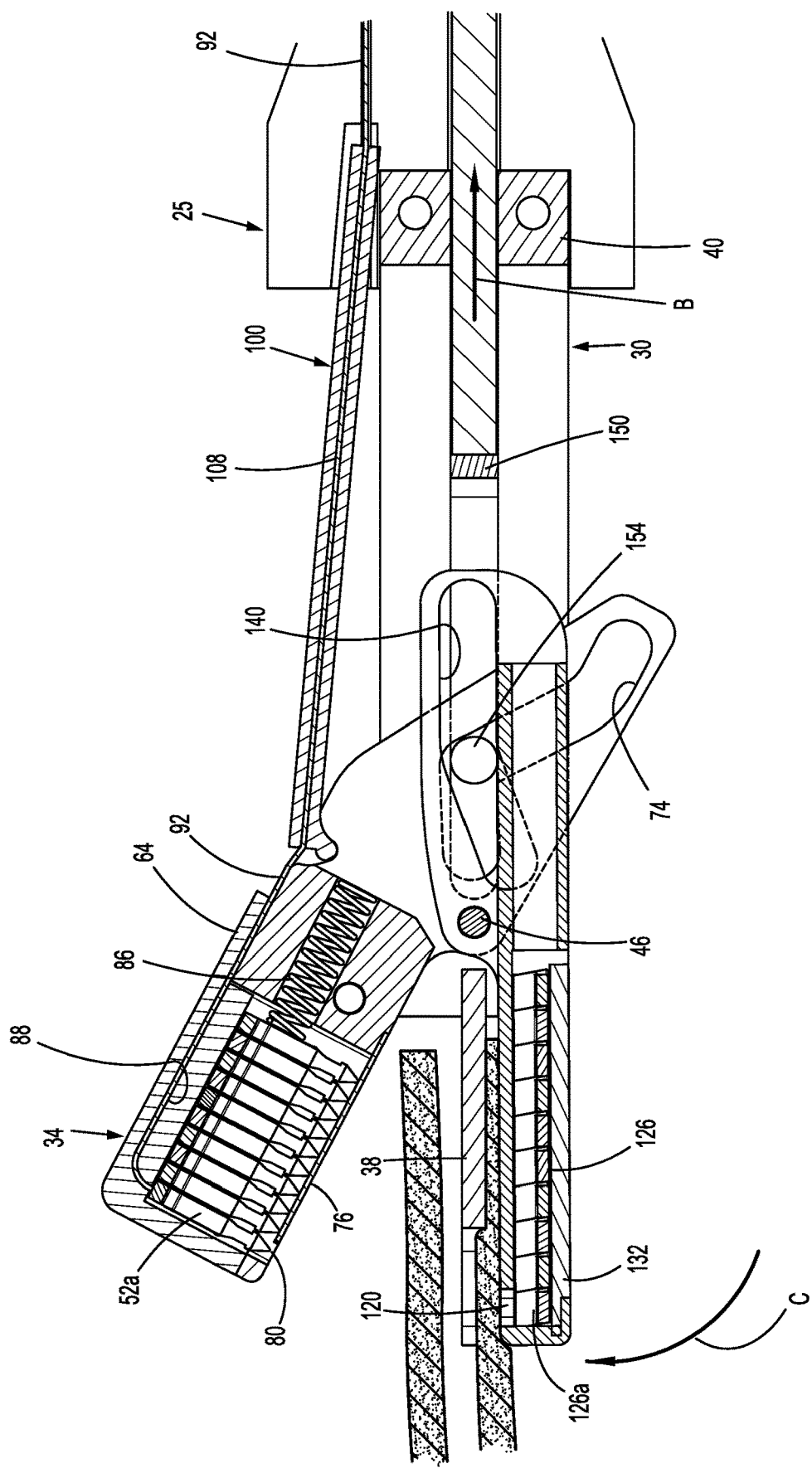
FIG. 12 is an enlarged view of the indicated area of detail shown in FIG. 11.

Referring to FIGS. 5-8, the clamping trigger 20 includes a body 162 that is pivotably supported between the half-sections 28a and 28b about a pivot member 164. The body 162 defines a channel 166 that receives an engagement portion 168 of the clamp rod 160. When the clamping trigger 20 is moved between a non-actuated position and an actuated position, the channel 166 is configured such that the clamp rod 160 is moved between its advanced and retracted positions to move the actuator 150 between its advanced and retracted positions. The body 162 includes a first grip loop 170 and a second grip loop 172. When a clinician grasps the first grip loop 170 and pulls the clamp trigger 20 towards the stationary handle 18, the clamp rod 160 and the actuator 150 are retracted from their advanced positions to their intermediate positions to move the bottom jaw 34 from the open position (FIG. 6) to the clamped position (FIG. 12). When the clinician grips the second grip loop 172 and pulls the clamp trigger 20 further towards the stationary handle 18, the clamp rod 160 and the actuator 150 are retracted from their intermediate positions to their retracted positions to move the top jaw 34 from the open position to the closed position.

Figure 10:
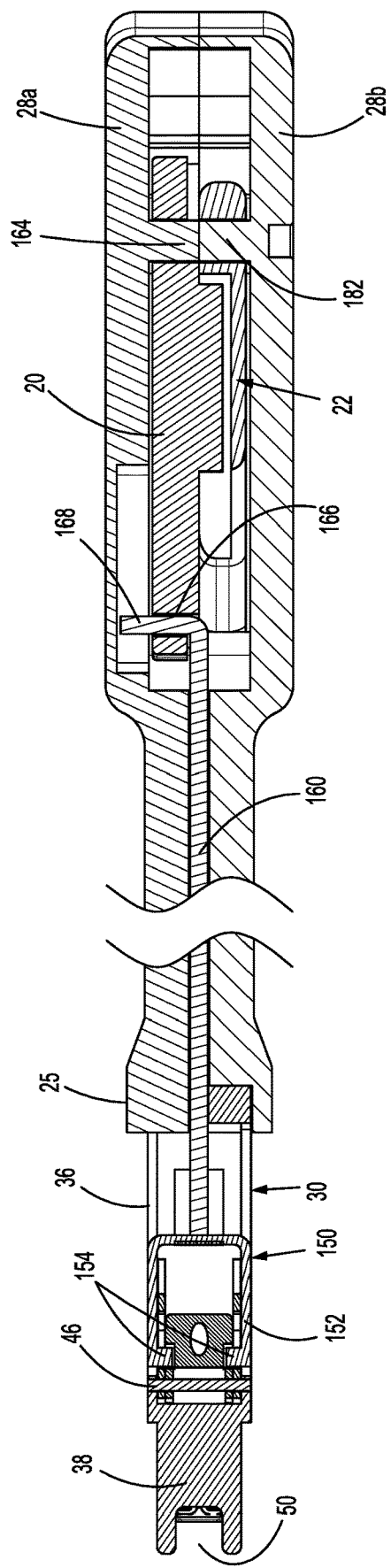
FIG. 10 is a cross-sectional view taken along section line 10-10 of FIG. 6.

The firing trigger 22 includes a body 180 that is pivotably supported between the half-sections 28a and 28b about a pivot member 182 (FIG. 10). The body 180 defines a channel 184 that receives an engagement portion 186 of the firing rod 94. When the firing trigger 22 is moved towards the stationary handle 18 between a non-actuated position and an actuated position, the channel 184 is configured such that the firing rod 94 is moved between retracted and advanced positions to move the staple pusher 92 between its retracted and advanced positions. As described above, when the staple pusher 92 is moved from its retracted position to its advanced position, a distal end of the staple pusher 92 engages the distal-most staple 52a in the top jaw 34 to drive the distal-most staple 52a from the receptacle 66, through the slot 80 in the top jaw 34, through the slot 50 in the stationary jaw 30, and through the slot 120 in the bottom jaw 32, into engagement with the distal-most staple retainer 126a to secure the staple 52a onto tissue "T" (FIG. 9).

Figure 8:
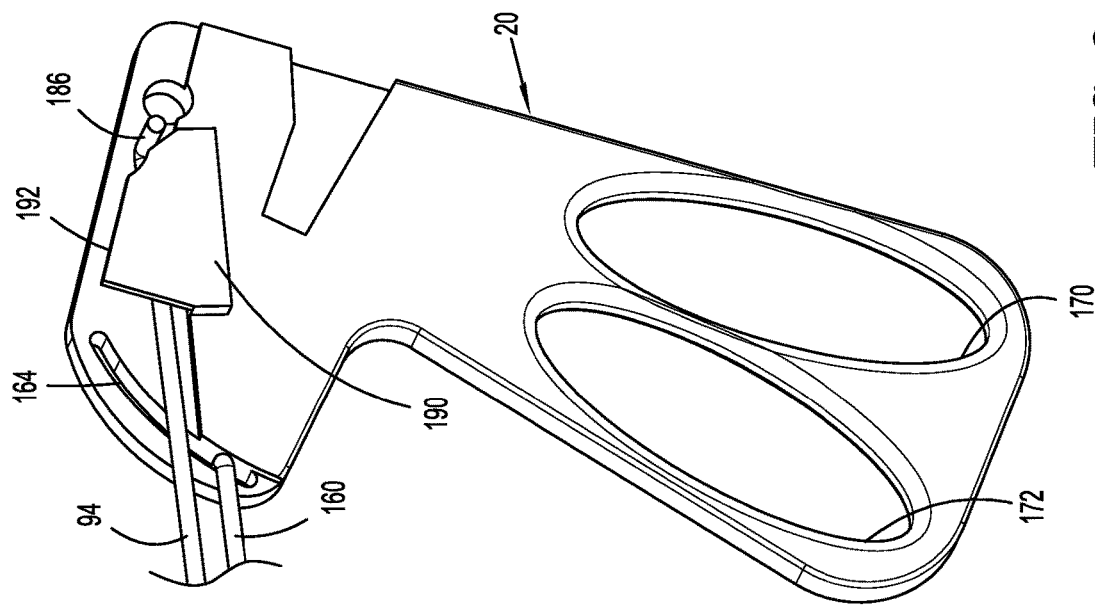
FIG. 8 is a side perspective view of the clamp trigger, a clamp rod, and a firing rod of the handle assembly shown in FIG. 7 with the firing rod locked out.
Figure 7:
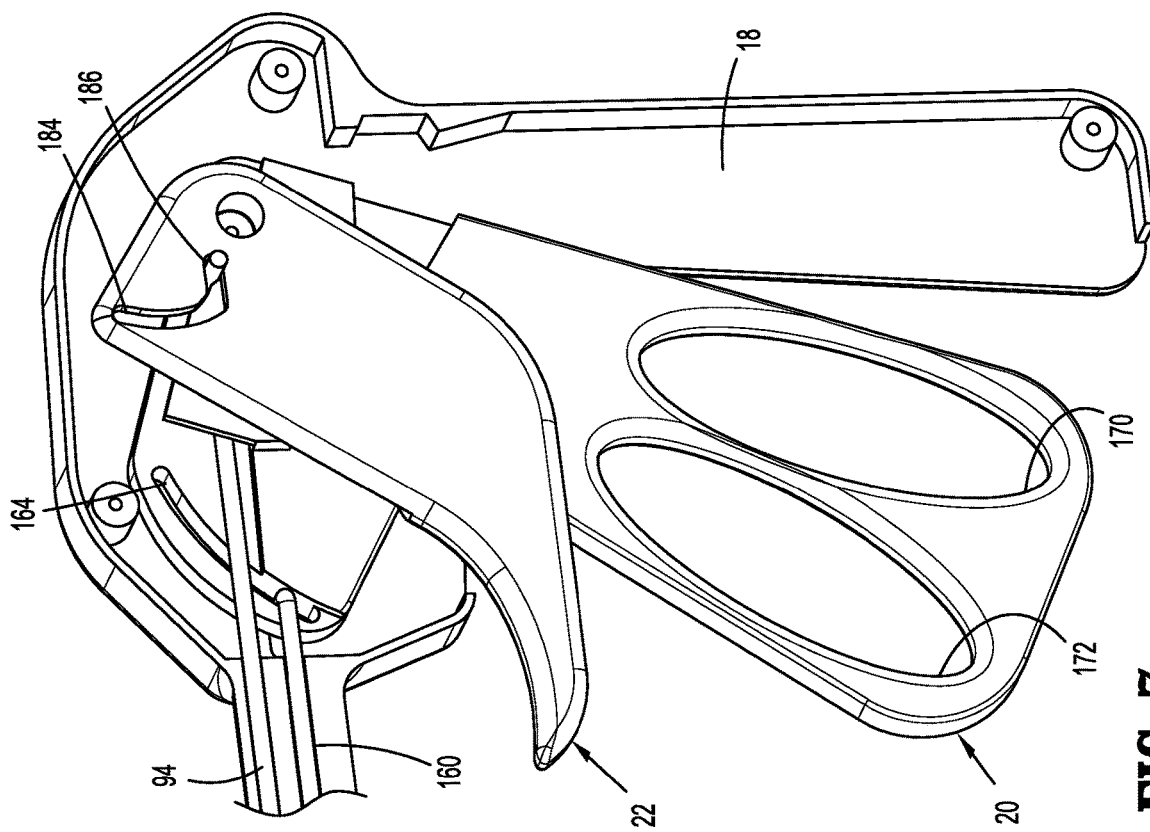
FIG. 7 is a side perspective view of a handle assembly of the stapling device shown in FIG. 1 with the clamp trigger and firing trigger in non-actuated positions.

Referring to FIG. 8, the clamping trigger 20 includes a lockout member 190 (FIG. 8). When the clamping trigger 20 is in the non-actuated position spaced from the stationary handle 18, the lockout member 190 is positioned to obstruct advancement of the engagement portion 186 of the firing rod 94 to prevent firing of the stapling device 10 when the top and bottom jaws 34 and 32 are in the open position. When the clamping trigger 20 is actuated, i.e., pivoted towards the stationary handle 18, the lockout member 190 is moved to a position in which the engagement portion 186 of the firing rod 94 can pass by the lockout member 190. In embodiments, the lockout member 190 includes a flat 192 that is rotated into alignment with the engagement portion 186 of the firing rod 94 when the clamping trigger 20 is fully actuated to facilitate advancement of the firing rod 94 to fire the distal-most staple 52. Thus, the stapling device 10 cannot be fired until the clamping trigger 20 is moved to the fully actuated position and the top and bottom jaws 34, 32 are in the clamped position (FIG. 14).

Referring to FIGS. 9 and 10, when the clamping trigger 20 is in the non-actuated position shown in FIG. 8, the top jaw 34 and the bottom jaw 32 are in their open positions spaced from the stationary jaw 30. In addition, the fingers 154 of the cam member 152 are positioned in the distal end of the cam slots 74 and 140 of the top and bottom jaws 34 and 32, respectively. As described above, the lockout member 190 on the clamping trigger 20 prevents actuation of the firing trigger 22 until the top and bottom jaws 34 and 32 are moved to their clamped positions. Thus, the staple pusher 92 is locked in its retracted position when the clamping trigger 20 is in its non-actuated position.

Figure 11:
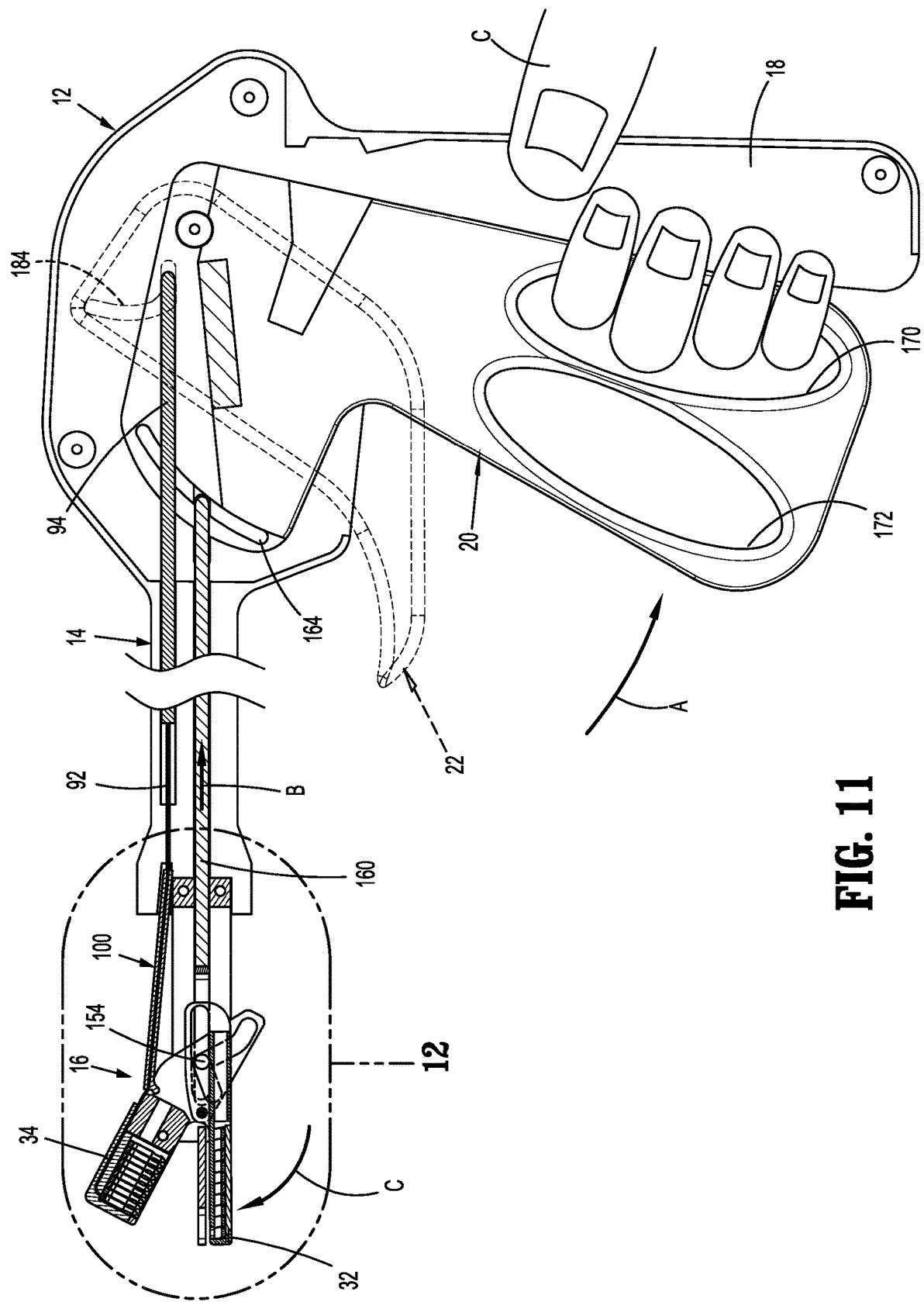
FIG. 11 is a side cross-sectional view of the stapling device shown in FIG. 1 with the top jaw in an open position and the bottom jaw in a clamped position and the clamp trigger in a partially actuated position.

Referring to FIGS. 11 and 12, when a clinician "C" grips the first grip loop 170 of the clamping trigger 20 and pivots the clamping trigger 20 towards the stationary handle 18 in the direction indicated by arrow "A" in FIG. 11 from a non-actuated position (FIG. 6) to an intermediate or partially actuated position, the clamp rod 160 is retracted from its advanced position (FIG. 9) in a direction indicated by arrow "B" to its intermediate position to retract the actuator 150 from its advanced position to its intermediate position. As the actuator 150 moves proximally towards its intermediate position, the fingers 154 of the actuator 150 move through the cam slots 74 and 140 of the top and bottom jaws 34 and 32 to pivot the bottom jaw 32 in the direction indicated by arrow "C" from the open position to the clamped position. As shown, movement of the actuator 150 from its advanced position to its intermediate position does not cause any substantial movement of the top jaw 34 in relation to the stationary jaw 30. In the intermediate position, the fingers 154 are positioned in a central portion of the cam slots 74 and 140.

Figure 13:
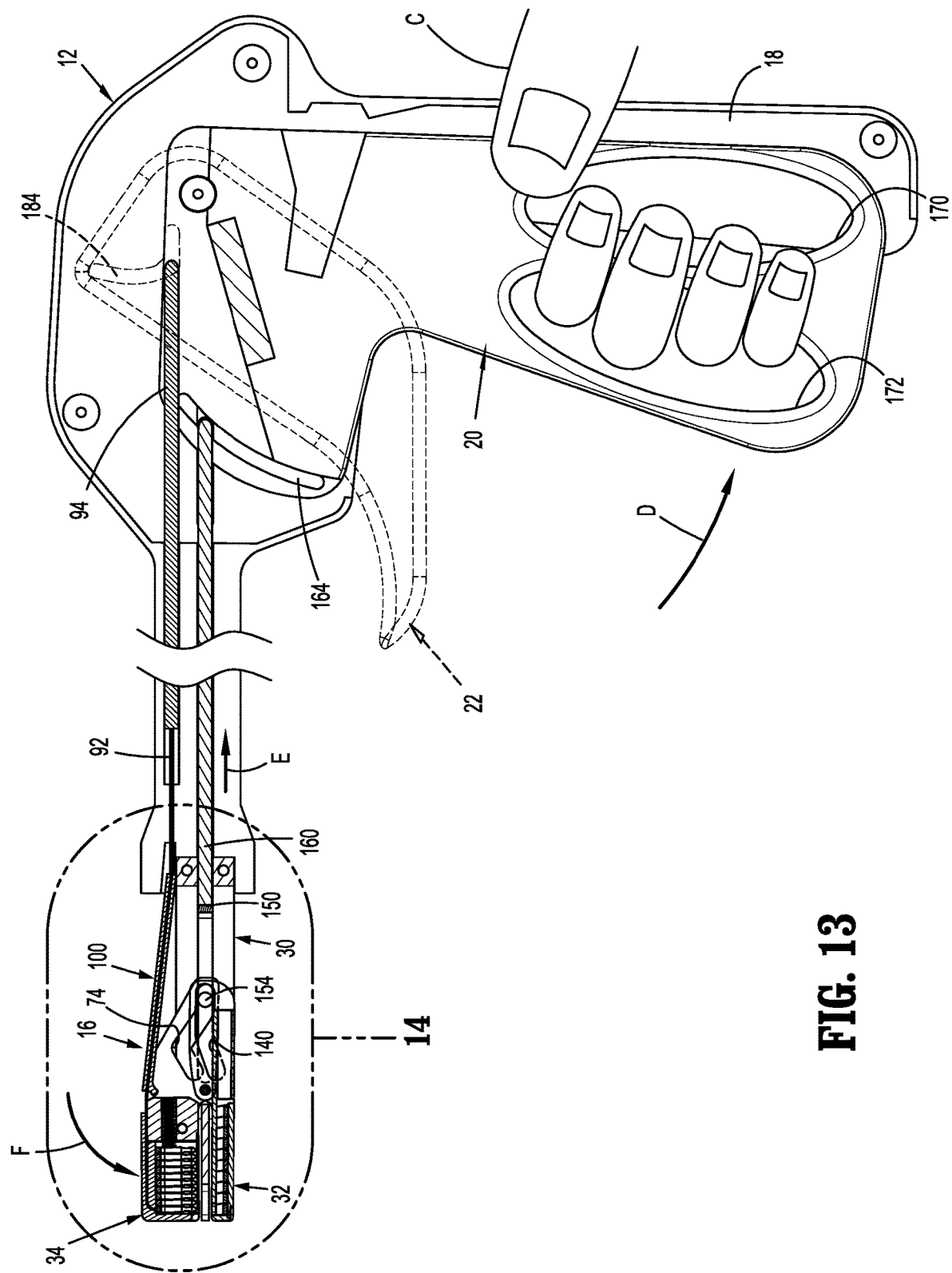
FIG. 13 is a side cross-sectional view of the stapling device shown in FIG. 11 with the top and bottom jaws in the clamped position and the clamp trigger in a fully actuated position.

Referring to FIGS. 13 and 14, when the clinician "C" grips the second loop 172 of the clamping trigger 20 and pivots the clamping trigger 20 towards the stationary handle 18 in the direction indicated by arrow "D" in FIG. 13, the clamp rod 160 is retracted from its intermediate position (FIG. 12) in a direction indicated by arrow "E" to its retracted position to retract the actuator 150 from its intermediate position to its retracted position. As the actuator 150 moves proximally towards its retracted position, the fingers 154 of the actuator 150 move further through the cam slots 74 and 140 of the top and bottom jaws 34 and 32 to pivot the top jaw 32 in the direction indicated by arrow "F" from the open position to the clamped position. As described above, as the top jaw 34 moves to the clamped position, the bottom jaw remains in the clamped position.

Referring to FIGS. 12 and 14, providing two jaws 32 and 34 that are independently movable in relation to a stationary jaw 30 between open clamped positions allows the clinician to move a first tissue section "T1" in relation to a second tissue section "T2" without the need of a grasper to facilitate joining of the tissue sections. More particularly, when the two tissue sections "T1" and "T2" to be joined are spaced from each other, the first tissue section "T1" can be clamped between the bottom jaw 32 and the stationary jaw 30 and pulled or moved towards the second tissue section "T2". When the first tissue section "T1" is repositioned adjacent the second tissue section "T2", the second tissue section "T2" can be clamped between the top jaw 34 and the stationary jaw 30. When the tissue sections "T1" and "T2" are both clamped between the bottom and top jaws 32 and 34 and the stationary jaw 30 as shown in FIG. 14, the firing trigger 22 can be actuated to staple the tissue sections "T1" and "T2" as described below.

Figure 16:
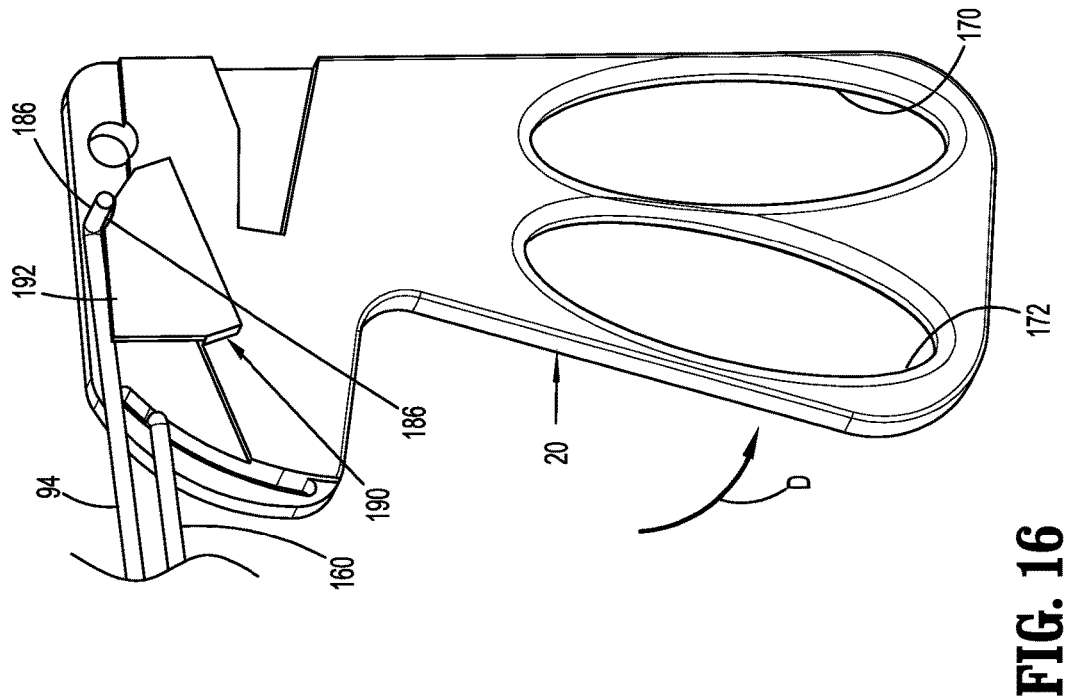
FIG. 16 is a side perspective view of the clamp trigger, a clamp rod, and a firing rod of the handle assembly shown in FIG. 15 with the firing rod unlocked.
Figure 15:
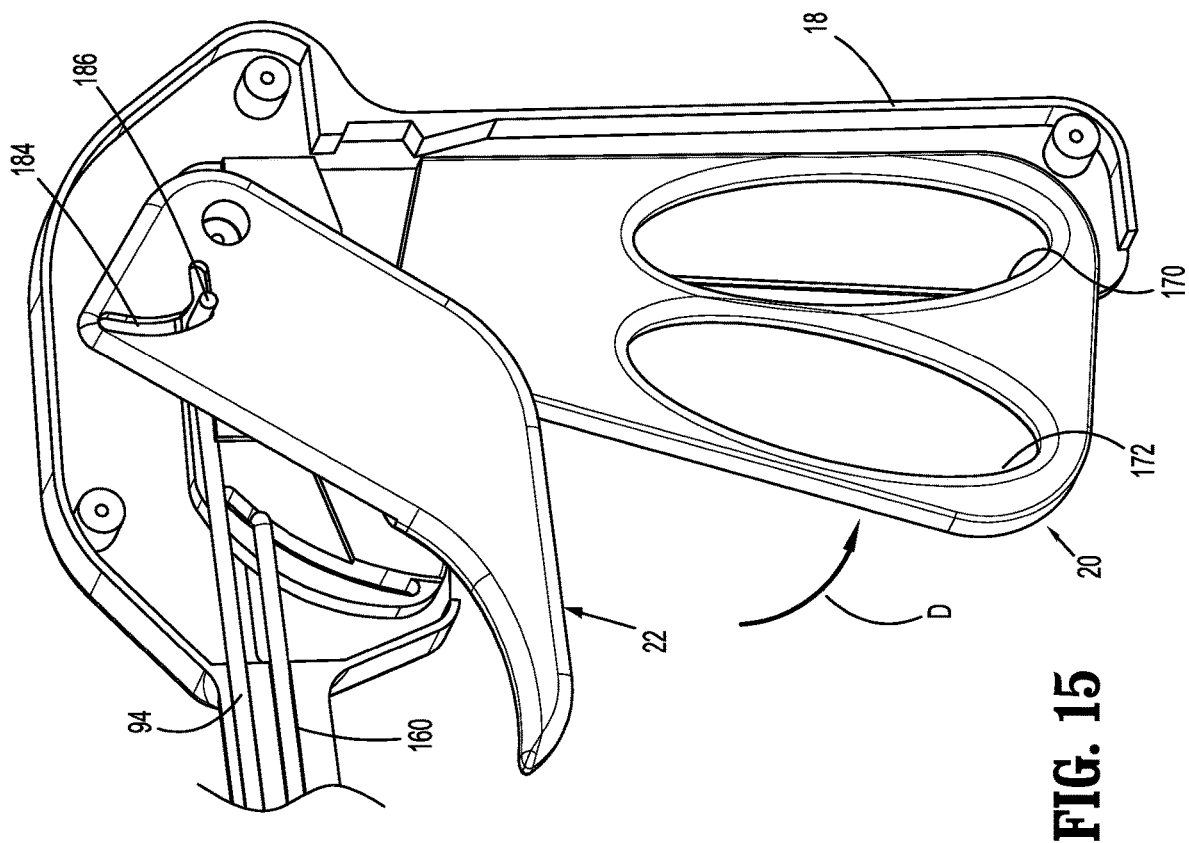
FIG. 15 is a side perspective view of a handle assembly of the stapling device shown in FIG. 13 with the clamp trigger in the fully actuated position and the firing trigger in the non-actuated position.

Referring to FIGS. 15 and 16, when the clamping trigger 20 is fully actuated by moving the clamping trigger 20 in the direction of arrow "A" (FIG. 11) as described above, the locking member 190 (FIG. 16) moves free of the engagement portion 186 of the firing rod 94. As such, the firing trigger 22 can be actuated to advance the firing rod 94 from the retracted position to the advanced position.

Referring to FIGS. 17 and 18, when the firing trigger 22 is pivoted from a non-actuated position towards an actuated position in the direction indicated by arrow "G" in FIG. 17, the engagement portion 186 of the firing rod 94 is driven distally to move the firing rod 94 in the direction indicated by arrow "H" in FIG. 17 from the retracted position towards the advanced position. As the firing rod 94 is moved towards its advanced position, the staple pusher 92 is moved towards its advanced position in the direction indicated by arrows "I" and moves through the channel 88. The distal end of the channel 88 is extends downwardly towards the distal-most staple 52a. The staple pusher 92 engages the staple 52a and drives the staple 52a from the receptacle 66 of the top jaw 34 through the slot 80 in the top jaw 34, through the tissue sections "T1" and "T2", and through the slot 120 in the bottom jaw 32 into engagement with the distal-most staple retainer 126 to secure the staple 52a to the tissue sections "T1" and "T2" and to secure the tissue sections "T1" and "T2" together.

After the stapling device 10 is fired, the triggers 20 and 22 can be returned to the non-actuated positions and the stapling device 10 can be used to perform a new surgical procedure or to complete surgical procedure being performed. This can be accomplished manually or using springs as is known in the art. It is noted after the distal-most staple 52a and the distal-most staple retainer 126a are secured to the tissue sections "T1" and "T2", the biasing members 86 and 134 urge the plurality of staples 52 and the plurality of staple retainers 126 distally to reposition a distal-most staple 52 and a distal-most staple retainer 126 in alignment with the slots 80 and 120 of the top and bottom jaws 34 and 32, respectively, to facilitate re-firing of the stapling device 10.

Persons skilled in the art will understand that the devices and methods specifically described herein and illustrated in the accompanying drawings are non-limiting exemplary embodiments. It is envisioned that the elements and features illustrated or described in connection with one exemplary embodiment may be combined with the elements and features of another without departing from the scope of the present disclosure. As well, one skilled in the art will appreciate further features and advantages of the disclosure based on the above-described embodiments. Accordingly, the disclosure is not to be limited by what has been particularly shown and described, except as indicated by the appended claims.

What is claimed is:

1. A surgical stapling device comprising:
   an elongate body having a distal portion and a proximal portion; and
   a tool assembly supported on the distal portion of the elongate body, the tool assembly including a stationary jaw, a top jaw positioned on one side of the stationary jaw, and a bottom jaw positioned on an opposite side of the stationary jaw, the top jaw being movable in relation to the stationary jaw independently of the bottom jaw between an open position and a clamped position, and the bottom jaw being movable in relation to the stationary jaw independently of the top jaw between an open position and a clamped position; and
   a clamp rod extending through the elongate body to the tool assembly, the clamp rod being movable to move the top jaw from the open position to the clamped position while the bottom jaw remains in the open position; wherein the top jaw supports a plurality of staples.

2. The surgical stapling device of claim 1, further including a staple pusher extending within the top jaw, the staple pusher being movable to eject a distal-most staple of the plurality of staples from the top jaw towards the bottom jaw.

3. The surgical stapling device of claim 2, wherein the bottom jaw supports a plurality of staple retainers, each of the plurality of staple retainers being engageable with a respective one of the plurality of staples to secure each of the plurality of staples to tissue.

4. The surgical stapling device of claim 1, further including an actuator that is operably associated with the top jaw, the actuator being movable from an advanced position towards a retracted position to move the top jaw from the open position to the clamped position.

5. The surgical stapling device of claim 4, wherein the actuator is operably associated with the bottom jaw, the actuator being movable to move the bottom jaw from the open position to the clamped position.

6. A surgical stapling device comprising:
   an elongate body having a distal portion and a proximal portion;
   a tool assembly supported on the distal portion of the elongate body, the tool assembly including a stationary jaw, a top jaw positioned on one side of the stationary jaw and supporting a plurality of staples, and a bottom jaw positioned on an opposite side of the stationary jaw, the top jaw being movable in relation to the stationary jaw independently of the bottom jaw between an open position and a clamped position, and the bottom jaw being movable in relation to the stationary jaw independently of the top jaw between an open position and a clamped position;
   an actuator operably associated with the top jaw and movable from an advanced position towards a retracted position to move the top jaw from the open position to the clamped position, and the actuator operably associated with the bottom jaw and movable to move the bottom jaw from the open position to the clamped position; and
   a clamp rod having a distal portion connected to the actuator, the clamp rod being movable from an advanced position to a retracted position to move the actuator from the advanced position to the retracted position.

7. The surgical stapling device of claim 6, wherein the top jaw includes a first camming slot, the bottom jaw includes a second camming slot, and the actuator includes a cam member, the cam member being movable within the first and second camming slots to move the top and bottom jaws from the open positions to the clamped positions.

8. The surgical stapling device of claim 7, wherein the first and second camming slots are configured such that movement of the actuator from the advanced position to an intermediate position moves the top jaw from the open position to the clamped position and movement of the actuator from the intermediate position to the retracted position moves the bottom jaw from the open position to the clamped position.

9. The surgical stapling device of claim 8, further including a handle assembly having a clamping trigger, the clamping trigger being connected to the actuator by the clamp rod, the clamping trigger being pivotable from a non-actuated position to a partially actuated position to move the top jaw from the open position to the clamped position and pivotable from the partially actuated position to a fully actuated position to move the bottom jaw from the open position to the clamped position.

10. The surgical stapling device of claim 9, further including a staple pusher extending within the top jaw, the staple pusher being movable from a retracted position to an advanced position to eject one of the plurality of staples from the top jaw into the bottom jaw.

11. The surgical stapling device of claim 10, wherein the handle assembly includes a firing trigger, the firing trigger being connected to the staple pusher by a firing rod, the firing trigger being movable from a non-actuated position to an actuated position to move the staple pusher from the retracted position to the advanced position.

12. The surgical stapling device of claim 11, wherein the clamping trigger includes a lock member, the lock member being positioned to prevent advancement of the firing rod until the clamping trigger is moved to the fully actuated position.

13. A method of performing a surgical procedure comprising:
positioning a tool assembly of a surgical device adjacent a first tissue segment such that the first tissue segment is positioned between a top jaw of the tool assembly and a stationary jaw of the tool assembly;
moving an actuator of the surgical device to move the top jaw towards the stationary jaw to clamp the first tissue segment between the top jaw and the stationary jaw;
moving the tool assembly towards a second tissue segment to move the first tissue segment towards the second tissue segment;
positioning the tool assembly of the surgical device adjacent the second tissue segment such that the second tissue segment is positioned between a bottom jaw of the tool assembly and the stationary jaw of the tool assembly;
moving the actuator of the surgical device to move the bottom jaw towards the stationary jaw to clamp the second tissue segment between the top jaw and the stationary jaw; and
moving a firing rod to eject a staple from the first jaw through the first and second tissue segments towards the second jaw to join the first tissue segment to the second tissue segment.

14. The method of claim 13, wherein moving the actuator of the surgical device to move the top jaw towards the stationary jaw includes moving the actuator from an advanced position to an intermediate position.

15. The method of claim 14, wherein moving the actuator of the surgical device to move the bottom jaw towards the stationary jaw includes moving the actuator from the intermediate position to a retracted position.

16. The method of claim 15, wherein moving the actuator of the surgical device from the advanced position to the intermediate position includes grasping a first grip loop of a clamp trigger of a handle assembly and pulling the first grip loop towards a stationary handle of the handle assembly.

17. The method of claim 16, wherein moving the actuator of the surgical device from the intermediate position to the retracted position includes grasping a second grip loop of the clamp trigger of the handle assembly and pulling the second grip loop towards the stationary handle of the handle assembly.

18. The method of claim 13, wherein moving the firing rod to eject the staple from the first jaw through the first and second tissue segments into the second jaw to join the first and second tissue segments includes moving a firing trigger of a handle assembly towards a stationary handle of the handle assembly to advance the firing rod to advance a staple pusher supported within the top jaw.

* * * * *